(12) United States Patent
Finkel et al.

(10) Patent No.: US 7,994,147 B2
(45) Date of Patent: Aug. 9, 2011

(54) CELLULAR GENES REGULATED BY HIV-1 INFECTION AND METHODS OF USE THEREOF

(75) Inventors: Terri H. Finkel, Wynnewood, PA (US); Jiyi Yin, Perrysburg, OH (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 12/172,731

(22) Filed: Jul. 14, 2008

(65) Prior Publication Data

US 2008/0293663 A1  Nov. 27, 2008

Related U.S. Application Data

(60) Division of application No. 11/057,484, filed on Feb. 14, 2005, now Pat. No. 7,405,292, which is a continuation-in-part of application No. 10/368,803, filed on Feb. 19, 2003, now Pat. No. 7,288,644.

(60) Provisional application No. 60/358,495, filed on Feb. 19, 2002.

(51) Int. Cl.
*A01N 43/04* (2006.01)
*A61K 31/70* (2006.01)

(52) U.S. Cl. ............................................. 514/44
(58) Field of Classification Search ............... 514/44
See application file for complete search history.

(56) References Cited

U.S. PATENT DOCUMENTS

| | | | |
|---|---|---|---|
| 6,228,585 B1 | 5/2001 | Dieckgraefe | |
| 6,455,674 B1 | 9/2002 | Einat et al. | |
| 6,555,667 B1 | 4/2003 | Einat et al. | |
| 6,716,432 B1 | 4/2004 | Paton et al. | |
| 7,655,788 B2* | 2/2010 | Khvorova et al. | 536/24.5 |
| 2006/0088836 A1* | 4/2006 | Wohlgemuth et al. | 435/6 |
| 2006/0240022 A1 | 10/2006 | Klippel-Giese et al. | |

FOREIGN PATENT DOCUMENTS

| WO | 99/09049 | 2/1999 |
|---|---|---|
| WO | 2004/035615 | 4/2004 |

OTHER PUBLICATIONS

Inoue et al. Journal of Drug Targeting 2006, vol. 14, No. 7, pp. 448-4550.*
Tuschl 2001, siRNA user guidelines, pp. 1-5.*
Harborth et al. (2001) J. Cell Science 114:4557-4565.*
Holen et al. (2002) Nucleic Acids Res. 30:1757-1766.*
U.S. Appl. No. 60/502,050, filed on Sep. 10, 2003.*
Abraham, R. T., et al. "TOR signaling: An odyssey from cellular stress to the cell growth machinery." Current Biology, 15(4): R139-R141 (2005).
Bakker, W. J., et al. "FOXO3a is Activated in Response to Hypoxic Stress and Inhibits HIF1-Induced Apoptosis via Regulation of CITED2." Molecular Cell, 28(6): 941-953 (2007).
Brugarolas, J., et al. "Regulation of mTOR function in response to hypoxia by REDD1 and the TSC1/TSC2 tumor suppressor complex." Genes and Development, 18(23): 2893-2904 (2004).
Corradetti, M. N., et al. "The stress-inducted proteins RTP801 and RTP801L are negative regulators of the mammalian target of rapamycin pathway." Journal of Biological Chemistry, 280(11): 9769-9772 (2005).
Ellisen, L. W. "Growth control under stress: mTOR regulation through the REDD1-TSC pathway." Cell Cycle, 4(11): 1498-1500 (2005).
Ellisen, L. W., et al. "REDD1, a developmentally regulated transcriptional target of p63 and p53, links p63 to regulation of reactive oxygen species." Molecular Cell, 10(5): 995-1005 (2002).
Han, E. S., et al. "The in vivo gene expression signature of oxidative stress." Physiological Genomics, 34(1): 112-126 (2008).
Schwarzer, R., et al. "REDD1 integrates hypoxia-mediated survival signaling downstream of phosphatidylinositol 3-kinase." Oncogene, 24(7): 1138-1149 (2005).
Sofer, A., et al. "Regulation of mTOR and cell growth in response to energy stress by REDD1." Molecular and Cellular Biology, 25(14): 5834-5845 (2005).
Wouters, B. G., et al. "Control of the hypoxic response through regulation of mRNA translation." Seminars in Cell and Developmental Biology, 16(4-5): 487-501 (2005).
Feit, et al., J. Pat. Trade. Off. Soc., 85:5-21 (2003).
Qiagen Product Guide 2001 pp. 40-51.
Lee et al. Nature Biotechnology 2002, vol. 19, pp. 500-505.
Samuel C Nature Biotechnology 2004, vol. 22, No. 3, pp. 280-282.
Novina et al. Nature medicine Jul. 2002, vol. 8, No. 7, pp. 681-686.
McManus et al. J. Immunol. 2002, vol. 169, pp. 5754-5760.
Kim, T.A., et al., "HIV-1 tat-mediated apoptosis in human brain microvascular endothelial cells," J. Immunol., 170:2629-2637, (2003).
Elbim, C., et al., "Redox and activation status of monocytes from human immunodeficiency virus-infected patients: relationship with viral load," J. Virology, 73:4561-4566, 1999.
Finzi, D. et al. "Identification of a Reservoir for HIV-1 in Patients on Highly Active Antiretroviral Therapy"; [EBSCO Host Research Databases] Science, vol. 278, 12 pgs, 1997.
Emerman, M. et al. "HIV-1 Regulatory/Accessory Genes: Keys to Unraveling Viral and Host Cel Biology"; [EBSCO Host Research Databases]Science, vol. 280:p. 1880, 5p.,1998.
Wong, J.K. et al. "Recovery of Replication-Competent HIV Despite Prolonged Suppression of Plasma Viremia"; [EBSCO Host Research Databases] Science, vol. 278:1297, 5p, 1997.
Corbeil, J. et al. "Temporal Gene Regulation During HIV-1 Infection of Human CD4+ T Cells"; Genome Research, 11: 1198-1204 (2001).
Diatchenko, L. et al. "Suppression subtractive hybridization: A method for generating differentially regulated or . . . "; Proc. Natl. Acad. Sci USA, 93: 6025-6030 (1996).

(Continued)

*Primary Examiner* — Brian Whiteman
(74) *Attorney, Agent, or Firm* — Dann Dorfman Herrell & Skillman; Robert C. Netter, Jr.

(57) ABSTRACT

This invention provides cellular gene products which have anti-apoptotic activity in HIV-1 infected cells and provides agents for the inhibition of the cellular gene products.

15 Claims, 23 Drawing Sheets

OTHER PUBLICATIONS

Geiss, G.K. et al. "Large-Scale Monitoring of Host Cell Gene Expression during HIV-1 Infection Using cDNA Microarrays"; Virology, 266: 8-16 (2000).

Ryo, A. et al. "Serial analysis of gene expression in HIV-1- infected T celllines";FEBS Letters, 462: 182-186(1999).

Simm, M. et al. "Cloning of differentially expressed genes in an HIV-1 resistant T cell clone by rapid subtraction hybridization, RaSH"; Gene, 269: 93-101 (2001).

Folks, T.M. et al. "Biological and Biochemical Characterization of a Cloned LEU-3-Cell Surviving Infection with the Acquired . . . "; J. Exp. Med. 164: 280-290 (1986).

Selliah, N. et al. "Cutting Edge: JAK3 Activation and Rescue of T Cells from HIV gp120-Induced Unresponsiveness"; The Journal of Immunology, 160: 5697-5701 (1998).

Scheuring, U.J. et al., "Differential expression profiles of apoptosis-affecting genes in HIV-infected cell lines and patient T cells"; AIDS, 13: 167-175 (1999).

Kinoshita, S. et al., "The T Cell Activation Factor NF-ATc Positively Regulates HIV-1 Replication and Gene Expression in T Cells"; Immunity, 6: 235-244 (1997).

Kinoshita, S. et al. "Host Control of HIV-1 Parasitism in T Cells by the Nuclear Factor of Activated T Cells"; Cell, 95: 595-604 (1998).

Cron, R.Q., et al. "NFAT1 Enhances HIV-1 Gene Expression in Primary Human CD4 T Cells"; Clinical Immunology, 94 (3): 179-191 (2000).

Nekhai, S. et al., "Cell Cycle-Dependent Stimulation of the HIV-1 Promoter by Tat-Associated CAK Activator"; Virology, 266: 246-256 (2000).

Liu, R. et al. "Homozygous Defect in HIV-1 Coreceptor Accounts for Resistance of Some Multiply-Exposed Individuals to HIV-1 Infection"; Cell, 86: 367-377 (1996).

Bushman, F. et al. "New developments in the biology and treatment of HIV"; PNAS, 95(19): 11041-11042 (1998).

Gelezlunas, R. et al. "HIV-1 Nef inhibits ASK1-dependent death signalling providing a potential mechanism for protecting the infected host cell"; Nature, 410: 834-838 (2001).

Hoxie, J.A. et al. "Persistent Noncytopathic Infection of Normal Human T Lymphocytes with AIDS-Associated Retrovirus"; Science, New Series, 229(4720): 1400-1402 (1985).

LaCasse, R.A et al. "Fusion-Competent Vaccines: Broad Neutralization of Primary Isolates of HIV"; [EBSCO Host Research Databases] Science, 0036-8075, vol. 283:357 6p. 1999.

Perrin, L. et al. "HIV Treatment Failure: Testing for HIV Resistance in Clinical Practice"; [EBSCO Host Research Databases], Science, vol. 280, Issue 5371, p. 1871, 3p, 1998.

Fauci, A.S. "Host factors and the pathogenesis of HIV-induced disease"; Nature, 384(6609): 529-534 (1996).

McMichael, AJ. et al. "Escape of Human Immunodeficiency Virus from Immune Control"; Annual Review of Immunology, 15(1): 271-296 (1997).

Chun, T. et al. "Presence of an inducible HIV-1 latent reservoir during highly active antiretroviral therapy"; Proc. Natl. Acad. Sci. USA, 94: 13193-13197 (1997).

Pantaleo, G. et al. "Immunopathogenesis of HIV Infection"; Annu. Rev. Microbiol., 50:825-54 (1996).

Rowland-Jones, S. et al. "New Insights into Host Factors in HIV-1 Pathogenesis"; Cell, 104: 473-476 (2001).

Nabel, G.J. "Challenges and opportunities for development of an AIDS vaccine"; Nature, 410: 1002-1007 (2001).

Landau, N.R. "HIV Recent advances in AIDS research: genetics, molecular biology and immunology"; Current Opinion in Immunology, 11 :449-450 (1999).

Ameisen, J.C. "Apoptosis subversion: HIV-Nef provides both armor and sword"; Nature Medicine, 7(11): 1181-1182 (2001).

Casella, C.R. et al. "Vpu Increases susceptibility of Human Immunodeficiency Virus Type 1-Infected Cells to Fas Killing"; Journal of Virology, 73(1): 92-100 (1999).

Shoshani, T. et al. "Identification of a Novel Hypoxia-Inducible Factor 1-Responsive Gene, RTP801, Involved in Apoptosis"; Molecular &Cellular Biology, 22(7): 2283-2293, 2002.

Lewis, J. et al. "Disruption of Hsp90 Function Results in Degradation of the Death Domain Kinase, Receptor-interacting Protein (RIP) . . . ," J.Biol.Chem., 275:10519-10526 (2000).

Pandey, P. et al. "Negative regulation of cytochrome c-mediated oligomerization of Apaf-1 and activation of procaspase-9 by heat shock protein 90";EMBO J., 19:4310-4322 (2000).

Galea-Lauri, J. et al. "Increased Heat Shock Protein 90 (hsp90) Expression Leads to Increased . . . ," The Journal of Immunology, 157: 4109-4118 (1996).

Swaroop, M. et al. "SAG/ROC2/Rbx2/Hrt2, a Component of SCF E3 Ubiquitin Ligase: Genomic Structure, a Splicing Variant . . . "; DNA and Cell Biology, 20(7): 425-434 (2001).

Duan, H. et al. "SAG, a Novel Zinc Ring Finger Protein That Protects Cells from Apoptosis Induced b Redox Agents"; Molecular and Cellular Biol., 194: 3145-3155 (1999).

Buck, et al., BioTechniques, 27(3):528-536, (1999).

Verma, et al., Nature 389:239-242, (1999).

Eck, et al., "Gene-based therapy," in: The pharmacological basis of therapeutics, Goodman and Gilman, eds., pp. 77-101, (1996).

Orkin, et al., "Report and recommendation of the panel to assess the NIH investment in research on gene therapy," NIH, (1995).

Change, et al., J. Biomedical Science, 7:322-333, (2000).

Parlato, et al., Cell Death and Differentiation, 7:37-47, (2000).

Yin, et al., AIDS 18:587-596, (2004).

Suarez-Alvarez, B., et al. "Characterisation of mouse monoclonal antibodies for pneumolysin: fine epitope mapping and V gene usage." Immunology Letters, 88: 227-239 (2003).

De Los Toyos, J. R., et al. "Functional Analysis of Pneumolysin by Use of Monoclonal Antibodies." Infection and Immunity, 64(2): 480-484 (Feb. 1996).

Hotze, E. M., et al. "Monomer-Monomer Interactions Drive the Prepore to Pore Conversion of a β-Barrel-forming Cholesterol-dependent Cytolysin." Journal of Biological Chemistry, 277(13): 11597-11605 (Mar. 29, 2002).

Salo, P., et al. "Mapping of Immunoreactive Sites of Pneumococcal Pneumolysin by Use of Synthetic Peptides." Infection and Immunity, 61(7): 2822-2826 (Jul. 1993).

* cited by examiner

Figure 5

```
CLUSTAL W (1.81) multiple sequence alignment

DA2              --------MPSLWDRFSSSST--------------------------------   13
BAA91214         --------MPSLWDRFSSSST--------------------------------   13
CAB66603         --------MPSLWDRFSSSST--------------------------------   13
BAB31006         --------MPSLWDRFSSSSS--------------------------------   13
AAF59841         MKMDVIAREQIIYGSLQGSNKNKDWTSRLPPP----------------------   32
AAF50074         MKMDVIAREQIIYGSLQGSNKNKDWTSRLPPP----------------------   32
AAF59840         MKMEVLSVQNHIQGKP-GVNKIKDWQASTAPLEEEEELTAGVNGNTAAGEGILDVDVVDG  59
BAB24676         ------------------------------------------------------

DA2              -SSSPSSLPRTPTPDR----PPRSAWGSATREEGFDRSTSLESSDCESLDSSNSGFGPEE  68
BAA91214         -SSSPSSLPRTPTPDR----PPRSAWGSATREEGFDRSTSLESSDCESLDSSNSGFGPEE  68
CAB66603         -SSSPSSLPRTPTPDR----PPRSAWGSATREEGFDRSTSLESSDCESLDSSNSGFGPEE  68
BAB31006         -SSSSS---RTPAADR----PPRSAWGSAAREEGLDRCASLESSDCESLDSSNSGFGPEE  65
AAF59841         -SAYTLDLMSKKAKTT----TGGSSNGSNATATSTTTSTSSSIKHKQPAGSSNNNVGQSQ  87
AAF50074         -SAYTLDLMSKKAKTT----TGGSSNGSNATATSTTTSTSSSIKHKQPAGSSNNNVGQSQ  87
AAF59840         HPASVLHMRQHQALNTRPSATPPSAGGGGPLAGGGSVGMTTPKQATSPVAAASFEAPLSG 119
BAB24676         --------MVATGSLSS------KNPASISELLDGGYHPGSLLSDFDYWDYVVPEPNLN---  45

DA2              DT------AYLDG----VSLPDFELLSDP---------------EDEHLCANLMQLLQ 101
BAA91214         DT------AYLDG----VSLPDFELLSDP---------------EDEHLCANLMQLLQ 101
CAB66603         DT------AYLDG----VSLPDFELLSDP---------------EDEHLCANLMQLLQ 101
BAB31006         DS------SYLDG----VSLPDFELLSDP---------------EDEHLCANLMQLLQ  98
AAF59841         SKKTKPSGSYNSN------SNYYYYAAD--EEEGGS---ADYALSNYDKKAVEELSLRLL 136
AAF50074         SKKTKPSGSYNSN------SNYYYYAAD--EEEGGS---ADYALSNYDKKAVEELSLRLL 136
AAF59840         GSAAAYHHAYMTNVLSSTAQQHHPLPASPLQSTAGARFGAADNLDDVSASAVRELSQQLQ 179
BAB24676         ---------------------------------EVVFEETTCQNLVKMLE  62

DA2              ESLAQARLGSRRPARLLMPSQLVSQVGKELLRLAYSEPCGLRGALLDVCVE-QGKSCHSV 160
BAA91214         ESLAQARLGSRRPARLLMPSQLVSQVGKELLRLAYSEPCGLRGALLDVCVE-QGKSCHSV 160
CAB66603         ESLAQARLGSRRPARLLMPSQLVSQVGKELLRLAYSEPCGLRGALLDVCVE-QGKSCHSV 160
BAB31006         ESLSQARLGSRRPARLLMPSQLVSQVGKELLRLAYSEPCGLRGALLDVCVE-QGKSCHSV 157
AAF59841         DELRAAKSRHLTCTEVSLPCDLTPSVAREIIRVSEKEPRGIRGCTTYIEPEDEPKNSRRI 196
AAF50074         DELRAAKSRHLTCTEVSLPCDLTPSVAREIIRVSEKEPRGIRGCTTYIEPEDEPKNSRRI 196
AAF59840         AQLRDAKRRHLACTEVTLPNDLTQRIAAEIIRMSEREPCGERACTLFIEFESEPNKVRRI 239
BAB24676         NCLSRSKQTKLGCSKVLVPEKLTQRIAQDVLRLSSTEPCGLRGCVMHVNLE-IENVCKKL 121
                   *     *   :. :.:* .*.  :.  :::::   **.*:  .  .* :   :  :

DA2              GQLALDPSLVPTFQLTLVLRLDSRLWPKIQGLFSSANSPFLPGFSQSLTLSTGFRVIKKK 220
BAA91214         GQLALDPSLVPTFQLTLVLRLDSRLWPKIQGLFSSANSPFLPGFSQSLTLSTGFRVIKKK 220
CAB66603         GQLALDPSLVPTFQLTLVLRLDSRLWPKIQGLFSSANSPFLPGFSQSLTLSTGFRVIKKK 220
BAB31006         AQLALDPSLVPTFQLTLVLRLDSRLWPKIQGLLSSANSSLVPGYSQSLTLSTGFRVIKKK 217
AAF59841         ASIKVDPDTVSTFEVYLTLRQDHRGWTSLLPQFMKS-----LAR--TITISPEYTITKNK 249
AAF50074         ASIKVDSDIVSTFEVYLTLRQDHRGWTSLLPQFMKS-----LAR--TITISPEYTITKNK 249
AAF59840         AYPKVDPTVSIFELYLTLRQDKSGWSSLVPQFIKN------LTRSNTINISPDFTLATKK 294
BAB24676         DRIVCDASVVPTFELTLVPFKQESCPWTSLKDFPFSRGR-PSSGLKRTLILSSGYRLVKKK 180
                  :  .  *  :.  * *. .    *..* *    :  . .:  :  :  ::   *:*

DA2              LYSSEQLLIEEC----------------  232
BAA91214         LYSSEQLLIEEC----------------  232
CAB66603         LYSSEQLPIEEC----------------  232
BAB31006         LYSSEQLLIEEC----------------  229
AAF59841         LYSADGLGARRSYSPGSHAHRPSAAIATPTN 280
AAF50074         LYSADGLGARRSYSPGSHAHRPSAAIATPTN 280
AAF59840         LYSSE-----------------------  299
BAB24676         LYSLIGTTVIEEC----------------  193
                 ***
```

Figure 6

```
ctgtcctcaccatgcctagcctttgggaccgcttctcgtcgtcgtccacctcct
cttcgccctcgtccttgccccgaactcccaccccagatcggccgccgcgctcagcctggg
ggtcggcgacccgggaggaggggtttgaccgctccacgagcctggagagctcggactgcg
agtccctggacagcagcaacagtggcttcgggccggaggaagacacggcttacctggatg
gggtgtcgttgcccgacttcgagctgctcagtgaccctgaggatgaacacttgtgtgcca
acctgatgcagctgctgcaggagagcctggcccaggcgcggctgggctctcgacgccctg
cgcgcctgctgatgcctagccagttggtaagccaggtgggcaaagaactactgcgcctgg
cctacagcgagccgtgcggcctgcggggggcgctgctggacgtctgcgtggagcagggca
agagctgccacagcgtgggccagctggcactcgaccccagcctggtgcccaccttccagc
tgaccctcgtgctgcgcctggactcacgactctggcccaagatccaggggctgtttagct
ccgccaactctcccttcctccctggcttcagccagtccctgacgctgagcactggcttcc
gagtcatcaagaagaagctgtacagctcggaacagctgctcattgaggagtgttgaactt
```

Figure 7

```
agcgtggtcgccgccgaggtaccttattattttttgttactgacagttaacagtggtgtgaca
tccagagagcagctgggctgctcccgccccagcccggcccagggtgaaggaagaggcacgtg
ctcctcagagcagccggagggagggggaggtcggaggtcgtggaggtggtttgtgtatctt
actggtctgaagggaccaagtgtgtttgttgtttgttttgtatcttgtttttctgatcggag
catcactactgacctgttgtaggcagctatcttacagacgcatgaatgtaagagtaggaagg
ggtgggtgtcagggatcacttgggatctttgacacttgaaaaattacacctggcagctgcgt
ttaagccttcccccatcgtgtacctgcccgggcggccgctcga
```

Figure 8

```
aggtacccatgctcacacacacacacttccagtttttatacaaatttttttaaaggaaagaaacca
acccaaagtattgcatttgaggtgacactccctgaagaatttttatacagaggtaatatactg
tttggcacagctgaaggttttttttattctttctttttttaaagtgagcccatgatttggtgt
ctttcccagattatcccctttgcgacaacacaagcaaaaatatttacaaaggtaaggcatag
tcaaactacataaagagaaaaaatcatgaggaaaatacatgaaaaagactaaagacttcgcc
ataacaaggtcttagtgataatagtgtccgtaaagatgtcatcagaattggtaaagtcaagc
atgctgcaaatatacccctttggattagaaaagagcacaatttttcttttttttgttttgttctg
ttttaagaagtggcatactgctctttctccctttggataatttctttttaagcccatcaaagg
aaaaaacaaacacaattcaaacaaacactgtcaagtgattcaagatcaaatatttacaataa
tcaaatggagtatcagatttttttttccaaactgataccacaaatacagagctgaaatctctc
tttggctcctctatatgcaaaattgaattagtcttcattgaagacaattatatagtcagttc
cagatgcaaaa
```

Figure 9

```
ttagcgtggtcgcggccgaggtacggtcgttgcccatggtgattaaagtgtggtt
atgggcaggaagacagactgtgtaaaaaggaatgacatcctggctcctcatctt
cttcatcagcaactaccataaccagtttgcgagtcaaatggcatttcctaacggc
aggcatggcggcccctgaaagacaacagctcccttttctgcttcggacaccactca
aacatttagacgcagctctatccttttcctagctagagaaggtgatgccttctt
ccattactcagagatgttgagacgttttcagaatttcttgttgaaatgaaaaaca
tcaagataaaggacgcctttcaggcattagctaaacttccacttcataactttcg
gcgagacatggtgagcctcctggtgtagagttcttttgtctttgtatggaatgac
tttttgctgtgatggttttgaatgttgggtttctgctgtctgcttagtacctgcc
cgggcggccgctcg
```

Figure 10

```
gcggccgaggtgacggagaggaaacctgcgccctggcctctcactccgggagctc
aggctccaagtcgggaggcgacaagatgttctccctcaagaagtggaacgcggtg
gccatgtggagctgggacgtggagtgcgatacgtgcgccatctgcagggtccagt
ggtctggggagaatgtaatcattccttccacaactgctgcatgtccctgtgggtg
aaacagaacaatcgntgccctctctgccagcaggactgggtggtccaaagaatcg
gcaaatgagagtggttagaaggcttcttancgcagttgttcagagccctggtgga
tcttgtaatccagtgccctacaaaggctagaacactacagggtcgtcttcgtcct
catcgccactctcctnanggatggcgacctgcccgggcggccgntcgaaagccga
attccagcac
```

Figure 11

```
acctctggcagttgggttcagggaaatgggattgncttggccttcaggctccttt
ggtcataattttaaaatatgggagtngaaaacaacnaagaatggaatggnctntt
aaaacaatgaaagagcntttatcgnttgnccttgaatgnanaatttgnttttga
tttcataattctgctggtaaatgngacngttaaaatgggccnttatgnatatata
ttataatttanaaatnccnttttataatttactattccagggngacntaatgca
tttaaatttgggatttgggnggngtnttatgtttaactggagttgncaagtntga
gtccctcangaaaaaaaaaattctnttttaaaaagcaatctgattcttagctnt
tgaaactnttgctncttaaatttccnataattaaaaatttaaaattttaaatta
gaattgccnatacttntacntttganaaggg
```

Figure 12

```
ggtcgcggccgatgtaccattgctttggccctgttagtgtcgcttgttggaggtttgcttta
tttgagaaggaacaacttggagttcatctataacaagactggttgggccatggtgtctctgt
gtatagtctttgctatgacttctggccagatgtggaaccatatccgtggacctccatatgct
cataagaacccacacaatggacaagtgagctacattcatgggagcagccaggctcagtttgt
ggcagaatcacacattattctggtacctgcccgggcggccgctcgaa
```

Figure 13

MPSLWDRFSS SSTSSSPSSL PRTPTPDRPP RSAWGSATRE EGFDRSTSLE SSDCESLDSS
NSGFGPEEDT AYLDGVSLPD FELLSDPEDE HLCANLMQLL QESLAQARLG SRRPARLLMP
SQLVSQVGKE LLRLAYSEPC GLRGALLDVC VEQGKSCHSV GQLALDPSLV PTFQLTLVLR
LDSRLWPKIQ GLFSSANSPF LPGFSQSLTL STGFRVIKKK LYSSEQLLIE EC

Fig. 15A

Identification (# Clones)

Cytoskeletal related/replication/transcription/translation (17)
Eukaryotic translation initiation factor 4E (1)  Annexin A (2)
Splicing factor (L10911.1) (1)  Matrin 3 (1)
Nucleosome assembly protein 1-like 1 (NAP1L1)  SnRNP (1)
Double-strand RNA binding protein (1)  Mitochondrial Fe-S protein (1)
Damage-specific DNA binding protein (1)  Poly A-binding protein (5)
Human mitochondrial protein (AF347015.1) (1)
Human initiation factor 2B epsilon (1)

Metabolism (11)
Spermidine synthase (1)  Dihydrofolate reductase (1)
Ubiquinol cytochrome C reductase (1)  MGAT2 (2)
Acyl-Co A-dehydrogenase (3)  NADH dehydrogenase (1)
Human isoleucine-tRNA synthetase (2)

Signal transduction/Cell regulation (26)
TRAF and TNFR-associated protein (1)  Lamin B receptor (1)
Protein tyrosine phosphatase, non-receptor type 4 (1)  SKB1 homolog (1)
Ubiquitin-conjugated enzyme 2A (1)  14-3-3 eta (1)
SH3-domain binding glutamic acid-rich protein (SH3 BGRL)(1)  HSP90 (1)
Phospholipase A2 Activating protein (1)  Rb-binding protein 8 (1)
Rb-binding protein 4 (1)  Tis11d (1)
Progesterone binding protein (1)  Prothymosin (1)
Host cell factor homolog (2)
Nuclear phosphoprotein (1)
Breast Carcinoma Metastasis Suppressor (1)
NEDD5 (1)
GAP-associated tyrosine phosphoprotein p62 (1)
RAD23B (2)
ADP-ribosylation factor-like 6 interacting protein (1)
Human UCC1 gene (1)
Human Karyopherin (importin) Beta 1 (1)
Ubiquitin-conjugating enzyme E2 (1)

Transcription factor (2)
Transcription factor 12 (2)

Functional unknown (19)
BC003500, BC007770, BC007103, XM_008278.3, XM_004883 (2), AF220049, AB046790 (3), NM_019895, AK027643, AK023109, XM_047707, BC002533, XM_039234, AK024221, XM_017998, XM_051909

Expressed sequence tags and genomic sequence (33)
HIV (8)

Fig. 15B

Identification (# Clones)

Cytoskeletal related/replication/transcription/translation (15)
Mitochondrial protein (4)
Actin-like protein (1)
HnRNP (3)
Transferrin receptor (1)
Human ribosomal protein L4 (1)
RNA polymerase I subunit 39 (2)
Human eukaryotic translation elongation factor $1\alpha 1$ (1)
Human ribosomal protein S25 (1)
Human histone family member Z (1)

Metabolism (4)
Glucosidase (1)
Threonyl-tRNA synthetase (1)
Human isoleucine-tRNA synthetase (1)
Glutamine synthetase (1)

Signal transduction/Cell regulation (15)
Herpesvirus associated ubiquitin specific protease (1)
CDK4 (4)
Human SYT interacting protein (1)
Protein disulfide isomerase-related (1)
Serine/threonine kinase 19 (2)
Human proteasome $\alpha 4$ (1)
Human calcium transport ATPase, type 2c, member 1 (ATP2c1) (1)
Cytohesin (1)
Human exportin (1)
CDC47(1)
Tumor suppressor (1)

Transcription factor (3)
NFAT4 (1)
MORF-related gene 15 (1)
Ring finger protein 7 (1)

Functional unknown (22)
AK000507, XM005991, BC000949, AF271994, AF161434, G214511, AK021519, BC003143, AJ132695, XM006135, BC001102, XM002133, XM011028, XM002079, XM002628
Chromosome 1 open reading frame 8 (C1ORF8), Human meiotic checkpoint regulator (2), FLJ2043, replication factor c (activator 1) 5, tumor differentially expressed 1 (TDE1), Disulfide isomerase-related protein P5

Expressed sequence tags and genomic sequences (19)
Vector (2)

CELLULAR GENES REGULATED BY HIV-1 INFECTION AND METHODS OF USE THEREOF

This application is a divisional application of U.S. application Ser. No. 11/057,484, filed on Feb. 14, 2005, now U.S. Pat. No. 7,405,292, which is a continuation-in-part of U.S. application Ser. No. 10/368,803, filed Feb. 19, 2003, now U.S. Pat. No. 7,288,644, which claims priority to US Provisional Application 60/358,495 filed Feb. 19, 2002. The foregoing applications are incorporated by reference herein.

Pursuant to 35 U.S.C. Section 202(c), it is acknowledged that the United States Government has certain rights in the invention described herein, which was made in part with funds from the National Institutes of Health Grant Nos. R01AI40003 and R01AI35513.

FIELD OF THE INVENTION

The present invention is related to HIV infection, and more specifically to the identification, purification, production and use of novel cellular genes, designated HALP (DA2), CD4, DF2, DF4, CC8 and DG1 for the development of novel therapeutic agents for the treatment of HIV infection.

BACKGROUND OF THE INVENTION

Several publications are referenced in this application by numerals in parentheses in order to more fully describe the state of the art to which this invention pertains. Full citations for these references are found at the end of the specification. Several patents and patent applications are also referenced in this application by number. The disclosure of each of these publications, patents, and patent applications is incorporated by reference herein.

Nearly twenty years have passed since the human immunodeficiency virus (HIV) was first identified as the causative agent of acquired immunodeficiency syndrome (AIDS). The human toll of this virus is tragic—almost 20 million people have died of AIDS, over 30 million are currently living with HIV, and 16,000 new infections occur daily. Still, there is neither a cure nor a proven therapy or vaccine for the treatment of HIV/AIDS.

Human immunodeficiency virus type-1 (HIV-1) infection is characterized by a host-virus relationship in which the virus utilizes the host cell's macromolecular machinery and energy supplies to produce progeny virus (1). Inevitably, after initial infection by HIV-1, the virus alters the host cell's physiological state, leading to disruption of immune responses, cell growth arrest and cell death (2). Specific viral and host cellular proteins are known to play crucial roles in this process (3). For example, the HIV-1 accessory proteins and host cell chemokine co-receptors, CCR5 and CXCR4, are essential for HIV-1 infection (4, 5, 6), and host cell target genes such as Ets-1, CDK4, NFAT1 and NFAT2, induce enhanced HIV-1 gene expression in vitro (7-11).

HIV-1 preferentially infects a class of immune cells called CD4$^+$ T cells or helper T cells which are essential to the function of the immune system. Following primary HIV-1 infection, the virus replicates in local lymph nodes and then disseminates in a massive viremia. Although HIV-1 elicits strong immune responses in most infected individuals, the virus almost invariably escapes immune containment (1, 2). Persistent HIV-1 infection is further characterized by a gradual decrease in CD4$^+$ T cells which leads to AIDS and ultimately death.

Analyses of T cells from individuals infected with HIV-1, or of T cells infected in vitro with HIV-1, indicate that a significant fraction of both infected and uninfected cells undergo programmed cell death or apoptosis. Apoptosis is a regulated form of cellular suicide that is critical to many physiological processes, including T cell development and normal immune function. However, the mechanisms of apoptosis in HIV-1 infection remain obscure and controversial. Analyses of lymphoid tissues from HIV-1 infected humans and SIV-1 (simian immunodeficiency virus) infected macaques suggest that most infected cells are not apoptotic and that the majority of apoptosis occurs in uninfected bystander cells (12). These data suggest that HIV-1 infected cells in vivo are relatively protected from or resistant to apoptosis.

Current therapies against HIV-1 infection are specific for targeting the virus. However, these therapies are not able to induce sustained suppression or cure of HIV because of HIV's ability to develop resistance to the treatment. Even when the amount of virus in the blood falls below the current limits of detection, HIV continues to reproduce at very low levels or alternatively, resides in a "reservoir" of latently infected T cells.

One treatment for HIV-1 infection is a cocktail of anti-viral drugs known as Highly Active Anti-Retroviral Therapy (or HAART) which includes two reverse transcriptase inhibitors and a protease inhibitor. HAART reduces the viral load in many patients to levels below the current limits of detection, but the rapid mutation rate of this virus limits the efficacy of this therapy (13). In addition, HAART is ineffective in some patients with HIV-1 infection and many more cannot tolerate its debilitating side effects.

Therapies for HIV-1 infection in the experimental stages of testing include the development of vaccines against HIV-1. Vaccines based on engineered gp120-CD4-CCR5 fusion proteins have been shown to elicit antibodies capable of neutralizing HIV-1 infectivity (14). Moreover, evidence of in vivo efficacy is not yet available and most researchers believe that a highly promising ideal vaccine candidate is not yet at hand (15).

Given the continuing impact of the HIV epidemic around the world and the lack of a proven therapy which provides sustained protection against HIV infection and AIDS, there remains a critical need for HIV research to identify new ways to prevent and treat this deadly disease.

SUMMARY OF THE INVENTION

This invention provides novel, biological molecules for identification, detection, and/or regulation of cellular molecules involved in HIV pathogenesis. Specifically, in one aspect of the invention, it has been discovered that the expression of certain previously uncharacterized cellular genes is related to inhibition of apoptosis in HIV-1 infected cells. Accordingly, the apoptosis modulators of the invention may be used to advantage in the development of therapeutic agents for the treatment of HIV infection and AIDS.

In a preferred embodiment of the invention, isolated nucleic acid molecules are provided which encode human apoptosis modulating proteins, DA2 (also referred to interchangeably herein as HIV-Associated Life Preserver (HALP) or DNA-damage-inducible transcript 4 (DDIT4)), CD4, DF2, DF4, CC8, and DG1. An exemplary HALP nucleic acid molecule of the invention comprises the sequence of SEQ ID NO: 1. The human CD4 nucleic acid has the sequence of SEQ ID NO: 15 (GenBank accession number AL049356). The human DF2 nucleic acid has the sequence of SEQ ID NO: 14 (Genbank accession number AF164679). The human DF4 has the nucleic acid sequence of SEQ ID NO: 13 (GenBank accession number BC039361). The human CC8 nucleic acid has the sequence of SEQ ID NO: 12. The human DG1 nucleic acid has the sequence of SEQ ID NO: 16.

According to another aspect of the present invention, an isolated nucleic acid molecule is provided, which has a sequence selected from the group consisting of: (1) SEQ ID NO: 1, SEQ ID NO: 12, SEQ ID NO: 13, SEQ ID NO: 14, SEQ ID NO: 15 and SEQ ID NO: 16; (2) a sequence specifically hybridizing with preselected portions or all of the complementary strand of SEQ ID NO: 1, SEQ ID NO: 12, SEQ ID NO: 13, SEQ ID NO: 14, SEQ ID NO: 15 and SEQ ID NO: 16; (3) a sequence comprising preselected portions of SEQ ID NO: 1, SEQ ID NO: 12, SEQ ID NO: 13, SEQ ID NO: 14, SEQ ID NO: 15 and SEQ ID NO: 16 (4) a complement of SEQ ID NO: 1, and (5) a sequence encoding part or all of a polypeptide encoded by the above-identified nucleic acid sequences. Such partial sequences are useful as probes to identify and isolate homologues of the apoptosis modulating nucleic acids of the invention. Accordingly, isolated nucleic acid sequences encoding natural allelic variants of the nucleic acids of SEQ ID NO: 1, SEQ ID NO: 12, SEQ ID NO: 13, SEQ ID NO: 14, SEQ ID NO: 15 and SEQ ID NO: 16 are also contemplated to be within the scope of the present invention.

Host cells comprising the apoptosis modulator-encoding nucleic acid molecules of the invention are also contemplated to be within the scope of the present invention. Such host cells include, but are not limited to: bacterial cells, fungal cells, yeast cells, plant cells, insect cells, human cells and other animal cells. The HALP-encoding nucleic acid molecules may be conveniently cloned into a plasmid or retroviral vector for introduction into host cells. Such cells are useful in screening methods to identify compounds which modulate HALP expression. Compounds so identified may have therapeutic value in the treatment of patients infected with HIV.

According to another aspect of the present invention, isolated human apoptosis modulating proteins are provided. The loss of expression of these proteins is correlated with increased or decreased apoptosis of HIV-1 infected cells. FIGS. 15 A and B set forth a series of pro-apoptotic and anti-apoptotic modulators, respectively, which can be employed in the screening methods described hereinbelow.

In another embodiment, the nucleic acid molecules of the invention may be used as diagnostic hybridization probes or as primers for diagnostic PCR analysis for identifying nucleic acids encoding apoptosis modulating proteins or mutations thereof. Antisense molecules are also provided herein and may be useful in the regulation of apoptosis modulator expression. Other methods encompassed by the present invention include immunodetection methods for assessing biological samples for the presence of apoptosis modulating protein.

According to another aspect of the invention, methods are provided for identifying agents which modulate (e.g., inhibit or activate) the activity of the apoptosis modulators described herein. The following summarizes methods employing the HALP encoding nucleic acid or protein, however any of the other apoptosis modulators of the invention, CC8, DF4, DF2, CD4 and DG1 may be employed in the following methods. An exemplary method comprises contacting cells expressing HALP, for example, with an agent suspected of having HALP-modulating activity under conditions whereby such an agent enters cells, and comparing apoptosis levels in cells in the presence and absence of the agent. Agents suspected of having HALP-modulating activity include, but are not limited to: an expression construct comprising HALP-encoding nucleic acid in an antisense orientation, an antisense HALP oligonucleotide, siRNA molecules engineered from the HALP sequence, antibodies immunologically specific for HALP which inhibit HALP function upon binding, and a variety of drugs and/or compounds. An increase in apoptosis in the presence of the agent is indicative of the agent's ability to inhibit HALP activity. A decrease in apoptosis in the presence of the agent is indicative of the agent's ability to activate HALP activity.

The screening methods described above may be practiced in HIV infected cells to identify those agents having antiviral activity. Antiviral activity can be assessed via termination or alteration in HIV particle or protein production levels in the presence and absence of such agents. Additionally, apoptosis in HIV infected cells can be measured in the presence and absence of such putative antiviral compounds.

The present invention also encompasses methods and compositions for the prevention and/or treatment of patients having diseases or conditions associated with aberrant apoptosis.

In yet another embodiment of the invention, small, interfering RNA (siRNA) molecules are provided which inhibit expression of HALP. Exemplary siRNA molecules have the sequences of SEQ ID NO: 21 and SEQ ID NO: 22.

Additionally, methods are provided for controlling expression of HALP in cells or tissues, e.g., human cells or tissues. The method comprises contacting cells or tissues with at least one siRNA molecule so that expression of HALP is altered. Alternatively, the at least one siRNA molecules may be encoded for in a vector which is brought into contact with the cells or tissue. Additionally, the siRNA molecules may be co-administered with at least one anti-HIV agent and/or at least one HIV vaccine.

In yet another embodiment of the invention, a pharmaceutical preparation is provided for treating a patient infected with HIV. The pharmaceutical preparation comprises at least one siRNA targeting HALP or at least one expression vector encoding for an siRNA targeting HALP. Such pharmaceutical preparations can be administered to a patient infected with HIV for treating the patient by eliminating or at least reducing the number of cells infected with HIV in the patient. The pharmaceutical preparations may additionally comprise at least one anti-HIV agent and/or at least one HIV vaccine.

BRIEF DESCRIPTION OF THE DRAWINGS

In FIG. 4A, lane 1 shows RNA expression from mock-infected cells, lane 2 shows RNA expression from day 7 post-infection cells, and lane 3 shows RNA expression from day 18 post-infected cells. GAPDH RNA expression was monitored as a control. In FIG. 4B, lane 1 shows RNA expression from mock-infected cells, lane 2 shows RNA expression from day 3 post-infection, lane 3 shows RNA expression from day 7 post-infection, lane 4 show RNA expression from day 11 post-infection, and lane 5 shows RNA expression from day 18 post-infection.

FIG. 5 shows the alignment of the amino acid sequence of DA2 (HALP; SEQ ID NO: 2) with two human proteins (GenBank accession numbers BAA91214 (SEQ ID NO: 2) and CAB66603 (SEQ ID NO: 3), two mouse proteins (GenBank accession numbers BAB31006 (SEQ ID NO: 4) and BAB24676 (SEQ ID NO: 5) and three fly proteins (GenBank accession numbers AAF59841 (SEQ ID NO: 6), AAF50074 (SEQ ID NO: 7) and AAF59840 (SEQ ID NO: 8).

FIG. 6 shows a nucleic acid encoding full length DA2 (HALP; SEQ ID NO: 1; 714 bp).

FIG. 7 shows a nucleic acid sequence of a partial DA2 (HALP) cDNA clone (SEQ ID NO: 9) isolated by subtractive hybridization and differential selection.

FIG. 8 shows a nucleic acid encoding CC8 (SEQ ID NO: 12) which was isolated by subtractive hybridization and differential selection.

FIG. 9 shows a nucleic acid encoding DF4 (SEQ ID NO: 13) which was isolated by subtractive hybridization and differential selection.

FIG. 10 shows a nucleic acid encoding DF2 (SEQ ID NO: 14) which was isolated by subtractive hybridization and differential selection.

FIG. 11 shows a nucleic acid encoding CD4 (SEQ ID NO: 15) which was isolated by subtractive hybridization and differential selection.

FIG. 12 shows a nucleic acid encoding DG1 (SEQ ID NO: 16) which was isolated by subtractive hybridization and differential selection.

FIG. 13 shows the amino acid sequence of DA2 (HALP; SEQ ID NO: 2).

FIGS. 14 B and C are graphs of the percentage of cells that were positive for GFP and p24 expression, respectively, over time.

FIGS. 15 A and B are tables of pro-apoptotic (FIG. 15A) and anti-apoptotic (FIG. 15B) molecules which may be screened using the methods of the invention. GenBank accession numbers are available for each of the listed genes and gene products.

DETAILED DESCRIPTION OF THE INVENTION

Figure 1:
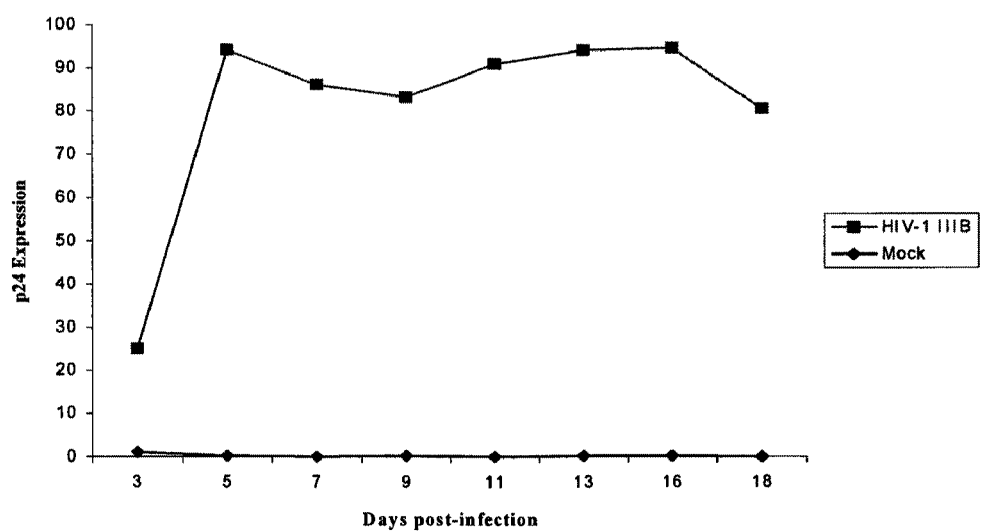
FIG. 1 shows a graph of p24 gag expression levels in CEM-SS cells mock-infected or infected with HIV-1 IIIB. Cells were collected at 2- or 3-day intervals post-infection and analyzed by flow cytometry.

Ground-breaking research in basic biology has led to an understanding of some of the pathogenic mechanisms of HIV-1 infection. Analysis of T cells from individuals infected with HIV-1, or of T cells infected in vitro with HIV-1, demonstrated that a significant fraction of both infected and uninfected cells undergo apoptosis. The mechanism(s) whereby HIV-1 infected cells undergo apoptosis, however, remain obscure. Additional research using lymphoid tissues from HIV-1 infected humans and SIV-1 infected macaques has suggested that most infected cells are not apoptotic, whereas uninfected bystander T cells are apoptotic (3). One possible explanation for this observation is that HIV-1 infection confers a selective advantage to infected cells, thus rendering such cells resistant to or protected from apoptosis. In addition, HIV-1 and host cellular targets may both be actively involved in the regulation of apoptosis during HIV-1 infection. Hence, the identification of viral and host cell-specific targets that modulate apoptosis in cells infected with HIV-1 is essential for elucidation of the mechanism(s) by which HIV-1 kills T cells. Such knowledge may be used to advantage to identify and provide agents (e.g., drugs, compounds) that induce apoptotic pathways in HIV-1 infected cells in patients.

To this end, a PCR-based subtractive hybridization method was applied to identify genes that play a role in modulating apoptosis in HIV-1 infected cells (Examples I and II of the present invention). Subtractive cloning is a powerful technique that facilitates isolation and cloning of mRNA transcripts which are differentially expressed in different cell populations. In general, a subtraction scheme involves a tracer (+) cell population and a driver (−) cell population and provides means to identify mRNA transcripts expressed in the tracer and not in the driver cell population. Briefly, nucleic acid (cDNA or mRNA) from a tracer cell population is allowed to hybridize with an excess of nucleic acid from a driver cell population to ensure that a high percentage of the tracer nucleic acid forms hybrids. Tracer/driver hybrids comprise nucleic acid sequences common to both cell populations. Hybrids comprised of complementary tracer and driver nucleic acid, and all the driver nucleic acid, are subsequently removed in a subtraction step. The remaining unhybridized fraction is enriched for those nucleic acid sequences expressed preferentially in the tracer cell population. Such methods are well known to those of skill in the art and have been described in detail elsewhere (e.g., Unit 5.9 of Ausubel et al.(27)).

As described herein and known in the art, reciprocal subtractions may be performed. Reciprocal subtractive hybridizations provide means to identify and isolate genes which are preferentially expressed in either of the different cell populations. Reciprocal subtractions may be used to isolate genes preferentially expressed in cell population A (used as a tracer) compared to B (used as a driver) and genes preferentially expressed in cell population B (used as a tracer) compared to A (used as a driver). Such methods utilize PCR to amplify cDNA after each subtraction to prepare sufficient quantities of tracer and driver nucleic acids for the next subtraction. The progress of the subtraction process may be monitored by a variety of means, including slot blot hybridization to detect residual levels of transcripts encoding housekeeping genes.

Differentially expressed cDNA sequences may be used to construct a subtracted cDNA library.

As described herein, a reciprocal subtractive hybridization was performed to identify genes preferentially expressed in HIV-1 infected cell populations undergoing apoptotis and to identify genes preferentially expressed in HIV-1 infected cell populations that are viable and stable (non-apoptotic). Genes preferentially expressed during apoptotic stages of HIV-1 infection are designated as having pro-apoptotic activity, whereas genes preferentially expressed during non-apoptotic stages of HIV-1 infection are designated as possessing anti-apoptotic activity. Additionally, a series of known pro-apoptotic and anti-apoptotic genes are provided in FIGS. 15A and B.

Thus, in accordance with the present invention, six novel host cell nucleic acids, designated HALP, CC8, DF4, DF2, CD4 and DG1 have been identified which regulate apoptosis in HIV-1 infected T cells. All of these nucleic acids and their encoded proteins are referred to herein collectively as apoptosis modulators and thus maybe utilized in the screening methods of the invention. Specifically, increases in apoptosis modulator levels are correlated with down-regulation or inhibition of apoptotic pathways in HIV-1 infected cells. Based on their expression pattern during the course of viral infection, therefore, the apoptosis modulators of the invention have been designated as having anti-apoptotic activity. Such apoptosis modulator mediated activity may have critical consequences in the development of viral latency. The apoptosis modulating compositions of the invention may be used to advantage to: (1) identify additional cellular targets that regulate HIV-1 infection; and (2) facilitate the development of novel therapeutic agents which inhibit the cellular activity of apoptosis modulators thereby promoting apoptosis of HIV-1 infected cells and preventing HIV-1 latency. Agents so developed may be used in combination with standard anti-retroviral therapy to ameliorate HIV-1 infection.

While HIV-1 is exemplified herein, the present invention encompasses method for screening agents having efficacy against other retroviruses, including without limitation HIV-2, simian immunodeficiency virus (SIV), and feline immunodeficiency virus (FIV).

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al. (28) or Ausubel et al. (27) are used.

I. Definitions

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, plastid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on. the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

Amino acid residues are identified in the present application according to the three-letter or one-letter abbreviations in the following Table:

TABLE I

| Amino Acid | 3-letter Abbreviation | 1-letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino acid of the mature protein sequence is designated as amino acid residue 1. As used herein, any amino acid residues associated with a mature protein not naturally found associated with that protein that precedes amino acid 1 are designated amino acid −1, −2, −3 and so on. For recombinant expression systems, a methionine initiator codon is often utilized for purposes of efficient translation. This methionine residue in the resulting polypeptide, as used herein, would be positioned at −1 relative to the mature HALP protein sequence.

A low molecular weight "peptide analog" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or non-mutated protein.

The present invention also includes active portions, fragments, derivatives and functional or non-functional mimetics of apoptosis modulator polypeptides, or proteins of the invention. An "active portion" of such a polypeptide means a peptide that is less than the full length polypeptide, but which retains measurable biological activity.

A "fragment" or "portion" of an apoptosis modulator polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the apoptosis modulator polypeptide sequence, antigenic determinants, or epitopes are useful for eliciting immune responses to a portion of the apoptosis modulator protein amino acid sequence for the effective production of immunospecific anti-HALP antibodies.

Different "variants" of the apoptosis modulator polypeptides exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include but are not limited to: (a) variants in which one or more amino acids residues are substituted with conservative or non-conservative amino acids, (b) variants in which one or more amino acids are added to the polypeptide, (c) variants in which one or more amino acids include a substituent group, and (d) variants in which the polypeptide is fused with another peptide or polypeptide such as a fusion partner, a protein tag or other chemical moiety, that may confer useful properties to the HALP-related polypeptide, such as, for example, an epitope for an antibody, a polyhistidine sequence, a membrane fusion sequence, a cytoplasmic targeting sequence, a nuclear targeting sequence, a biotin moiety and the like. Other apoptosis modulator polypeptides of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art. To the extent such allelic variations, analogues, fragments, derivatives, mutants, and modifications, including alternative nucleic acid processing forms and alternative post-translational modification forms, result in derivatives of the apoptosis modulator polypeptides that retain any of the biological properties of the apoptosis modulators, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen, such as epitopes of an apoptosis modulator protein. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')$_2$ and F(v).

As used herein, the terms "inhibiting", "reducing" or "preventing" apoptosis modulator activity are intended to mean a reduction in apoptosis modulator mediated anti-apoptotic activity which results in an increase in cell death or a reduction in the survival time of a cell. Such terms are also intended to mean an increase in the appearance or an acceleration in the appearance of morphological and/or biochemical changes normally associated with apoptosis. Thus, this invention provides compositions and methods to decrease survival time and/or survival rate of a cell or population of cells (e.g., HIV-1 infected cells) which, absent the use of the method, would normally be expected to live. Accordingly, the present invention also provides compositions and methods to prevent and/or treat diseases or pathological conditions associated with resistance to apoptotic pathways in a subject.

As used herein, the terms "promoting", "inducing" or "enhancing" apoptosis modulator activity are intended to mean an increase in apoptosis modulator anti-apoptotic activity which results in a decrease in cell death or prolongation in the survival time of the cell. Such terms are also intended to mean a diminution in the appearance or a delay in the appearance of morphological and/or biochemical changes normally associated with apoptosis. Thus, this invention provides compositions and methods to increase survival time and/or survival rate of a cell or population of cells which, absent the use of the method, would normally be expected to die. Accordingly, the present invention also provides compositions and methods to prevent and/or treat diseases or pathological conditions associated with unwanted cell death in a subject.

As used herein, the term "anti-apoptotic" refers to the ability of a molecule (e.g., protein, nucleic acid, or drug) to inhibit the induction and/or progression of apoptosis in a cell in vitro or in vivo. As used herein, "anti-apoptotic activity" refers to the functional properties of a molecule which confer the ability to inhibit the induction and/or progression of cellular apoptosis.

As used herein, the term "pro-apoptotic" refers to the ability of a molecule (e.g., protein, nucleic acid, or drug) to promote or enhance the induction and/or progression of apoptosis in a cell in vitro or in vivo.

As used herein, "pro-apoptotic activity" refers to the functional properties of a molecule which confer the ability to promote the induction and/or progression of cellular apoptosis. As used herein, the term "inordinate cellular apoptosis" refers to an in vitro or in vivo state or condition in which an excessive or elevated degree of apoptosis exists.

As used herein, the term "unsubtracted tester" refers to cDNA derived from the tester cell population that contains specific (differentially expressed) transcripts.

As used herein, the term "unsubtracted driver" refers to cDNA derived from the driver cell population which comprises a reference cDNA population against which differentially expressed transcripts derived from the tester cell population may be compared by subtractive hybridization.

As used herein, and particularly with regard to the methodology of subtractive hybridization and differential screening, the term "probe" refers to DNA or RNA fragments which may be labeled with a radioactive isotope or non-radioactive reagents. Such sequences recognize specific DNA sequences and are of utility in hybridization reactions.

As used herein, the term "unsubtracted tester probe" refers to the plurality of probes derived from the unsubtracted tester cDNA population.

As used herein, the term "unsubtracted driver probe" refers to the plurality of probes derived from the unsubtracted driver cDNA population.

As used herein, the term "forward subtracted probe" refers to the plurality of probes remaining in the tester cDNA population after probes conserved between the unsubtracted driver and unsubtracted tester cDNA populations are removed from the tester cDNA population. In brief, a "forward subtracted probe" may be produced as follows: tester and driver mRNA populations are converted into cDNA; tester and driver cDNA are hybridized and the hybrid sequences are removed; the remaining unhybridized cDNAs represent genes that are preferentially expressed in the tester, but are absent from or low in driver cDNA.

As used herein, the term "reverse subtracted probe" refers to the plurality of probes remaining after subtractive hybridization is performed with the original tester cDNA as a driver and the original driver cDNA as a tester. The remainder of the method is identical to that for production of "forward subtracted probe".

II. Preparation of Apotosis Modulator Encoding Nucleic Acid Molecules

In accordance with the present invention, six cellular genes have been identified with are involved in regulation of apoptosis in HIV infected cells. While the following exemplifies preparation of HALP encoding nucleic acids, any of the other nucleic acid molecules encoding the apoptosis modulators described herein, CC8, DF2, DF4, DG1, and CD4 may be prepared in a comparable manner.

A full length nucleic acid sequence encoding HALP (SEQ ID NO: 1; 714 bp) is shown in FIG. 6. The full length cDNA was generated based on reverse transcription polymerase chain reaction (RT-PCR) utilizing HALP-specific primers CTG TCC TCA CCA TGC CTA (SEQ ID NO: 10; 5' primer) and TGA AGT TCA ACA CTC CTC AA (SEQ ID NO: 11; 3' primer) whose sequences were based on those of a partial HALP nucleic acid (SEQ ID NO: 9; 415 bp; FIG. 7) isolated by subtractive hybridization. All sequences were determined using ABI PRISM® BigDye™ Primer Cycle Sequencing Kits at the Nucleic Acid/Protein Core in The Children's Hospital of Philadelphia utilizing routine methodology.

Nucleic acid molecules of the invention encoding apoptosis modulator polypeptides may be prepared by two general methods: (1) synthesis from appropriate nucleotide triphosphates, or (2) isolation from biological sources. Both methods utilize protocols well known in the art. The availability of nucleotide sequence information, such as the DNA sequences encoding HALP, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

Specific probes for identifying such sequences as the apoptosis modulator encoding sequence may be between 15 and 40 nucleotides in length. For probes longer than those described above, the additional contiguous nucleotides are provided within the corresponding SEQ ID NO.

Additionally, cDNA or genomic clones having homology with apoptosis modulators may be isolated from other species, including without limitation feline and simian species, using oligonucleotide probes corresponding to predetermined sequences within the apoptosis modulator nucleic acids of the invention. Such homologous sequences encoding apoptosis modulators may be identified by using hybridization and washing conditions of appropriate stringency. For example, hybridizations may be performed, according to the method of Sambrook et al. (28) using a hybridization solution comprising: 5× SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2× SSC and 1% SDS; (2) 15 minutes at room temperature in 2× SSC and 0.1% SDS; (3) 30 minutes-1 hour at 37° C. in 1× SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology (28) is as follows:

$$T_m = 81.5° C. + 16.6 \text{Log}[Na+] + 0.41(\% G+C) - 0.63 (\% \text{formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6× SSC, 5× Denhardt's solution, 0.5% SDS and 100 µg/ml denatured salmon sperm DNA at 42° C., and washed in 2× SSC and 0.5% SDS at 55° C. for 15 minutes. A high stringency hybridization is defined as hybridization in 6× SSC, 5× Denhardt's solution, 0.5% SDS and 100 µg/ml denatured salmon sperm DNA at 42° C., and washed in 1× SSC and 0.5% SDS at 65° C. for 15 minutes. A very high stringency hybridization is defined as hybridization in 6× SSC, 5× Denhardt's solution, 0.5% SDS and 100 µg/ml denatured salmon sperm DNA at 42° C., and washed in 0.1× SSC and 0.5% SDS at 65° C. for 15 minutes.

The nucleic acid molecules described herein include cDNA, genomic DNA, RNA, and fragments thereof which may be single- or double-stranded. Thus, nucleic acids are provided having sequences capable of hybridizing with at least one sequence of a nucleic acid sequence, such as selected segments of a sequence encoding an apoptosis modulator. Also contemplated in the scope of the present invention are methods of use for oligonucleotide probes which specifically hybridize with the DNA from the sequences encoding the apoptosis modulators under high stringency conditions. Primers capable of specifically amplifying the sequences encoding apoptosis modulators are also provided. As mentioned previously, such oligonucleotides are useful as primers for detecting, isolating and amplifying sequences encoding apoptosis modulators.

Antisense nucleic acid molecules which may be targeted to translation initiation sites and/or splice sites to inhibit the expression of the apoptosis modulator genes or production of their encoded proteins are also provided. Such antisense molecules are typically between 15 and 30 nucleotides in length and often span the translational start site of mRNA molecules. Antisense constructs may also be generated which contain the entire apoptosis modulator sequence in reverse orientation.

Small interfering RNA (siRNA) molecules designed to inhibit expression of the apoptosis modulator genes are also provided. Typically, siRNA molecules are double-stranded RNA molecules between about 12 and 30 nucleotides in length, more typically about 21 nucleotides in length. The nucleotide sequence of the siRNA molecules commonly begin from an AA dinucleotide sequence near the AUG start codon but not within about 75 bases of said start codon. The siRNA molecules typically have a GC content of between about 45% and about 55% and ideally do not contain stretches of more than 3 guanosine bases in a row.

III. Preparation of Apotosis Modulating Proteins and Antibodies Immunologically Specific Therefore The apoptosis modulators of the present invention may be prepared in a variety of ways, according to known methods. The proteins may be purified from appropriate sources, e.g., human cells or tissues as described in detail in Example 1.

The identification of nucleic acid molecules encoding apoptosis modulators facilitates the expression of apoptosis modulators in vitro by methods known in the art. For example, a cDNA or gene may be cloned into an appropriate in vitro transcription vector, such as a pSP64 or pSP65 vector for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of apoptosis modulators may be produced by expression in a suitable procaryotic or eucaryotic system. For example, part or all of a DNA molecule may be inserted into a plasmid vector adapted for expression in a bacterial cell (such as E. coli) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, translation control sequences and, optionally, enhancer sequences.

The apoptosis modulator protein produced by gene expression in a recombinant procaryotic or eucaryotic system may be purified according to methods known in the art. In a preferred embodiment, the recombinant protein contains several (e.g., 6-8) histidine residues on the amino or carboxyl termini, which allows the protein to be affinity purified on a nickel column. If histidine tag-vectors are not used, an alternative approach involves purifying the recombinant protein by affinity separation, such as by immunological interaction with antibodies that bind specifically to the recombinant protein. Such methods are commonly used by skilled practitioners.

Apoptosis modulator protein, prepared by the aforementioned methods, may be analyzed according to standard procedures. Methods for analyzing the HALP-inhibitory activity of apoptosis are set forth in U.S. Pat. Nos. 5,976,786 and 6,046,007, the disclosures of which are incorporated by reference herein.

The present invention also provides antibodies capable of immunospecifically binding to proteins of the invention. Polyclonal or monoclonal antibodies immunologically specific for epitopes of apoptosis modulators may be prepared according to standard methods. Monoclonal antibodies may be prepared according to general methods of Köhler and Milstein, following standard protocols. Polyclonal and/or monoclonal antibodies may be prepared as described in several laboratory protocol handbooks, including: Sambrook et al.(28); Ausubel et al. (27), and Harlow and Lane (29). In a preferred embodiment, antibodies are prepared, which react immunospecifically with various epitopes of the apoptosis modulators of the invention.

Polyclonal or monoclonal antibodies that immunospecifically interact with the apoptosis modulators may be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Antibodies may also be used to bind an apoptosis modulator molecule, thereby rendering the apoptosis modulator inactive and/or unstable. Antibodies capable of binding to apoptosis modulators and inhibiting apoptosis modulator function are known as inhibitory antibodies. Such apoptosis modulator inhibitory antibodies may be used to advantage to induce apoptosis in HIV-1 infected cells in vitro and in vivo. Such apoptosis modulator inhibitory antibodies are of particular utility for the therapeutic treatment of HIV-1 patients to facilitate induction of apoptosis in HIV-1 infected cells, thus eradicating such cells from the patient.

IV. Uses of Apotosis Modulators Encoding Nucleic Acid Molecules, Proteins and Antibodies A. Nucleic Acids Encoding Apoptosis Modulators Nucleic acids encoding apoptosis modulator protein may be used for a variety of purposes in accordance with the present invention. DNA, RNA, or fragments thereof encoding apoptosis modulators may be used as probes to detect the presence of and/or expression of such genes. Methods in which nucleic acids encoding apoptosis modulators may be utilized as probes for such assays include, but are not limited to: (1) in situ hybridization; (2) Southern hybridization (3) Northern hybridization; and (4) assorted amplification reactions such as polymerase chain reactions (PCR).

The nucleic acids of the invention may also be utilized as probes to identify related genes from other animals and microbes. As is well known in the art, hybridization stringencies may be adjusted to allow hybridization of nucleic acid probes with complementary sequences of varying degrees of homology.

Nucleic acid molecules, or fragments thereof, encoding apoptosis modulators may also be utilized to control the production of apoptosis modulators, thereby regulating the amount of protein available to participate in the inhibition of apoptosis in HIV-1 infected cells. As mentioned above, antisense oligonucleotides corresponding to essential processing sites in apoptosis modulator mRNA molecules, siRNA molecules, or other gene silencing approaches may be utilized to inhibit apoptosis modulator production in targeted cells, such as T cells. Alterations in the physiological amount of apoptosis modulators may dramatically affect the activity of other protein factors involved in the induction or maintenance of retroviral infection including HIV-1, HIV-2, FIV, and SIV infections.

The nucleic acid molecules of the invention may also be used to advantage to identify mutations in apoptosis modulator encoding nucleic acids from HIV-1 infected cells. Nucleic acids may be isolated from HIV-1 infected patients and contacted with the sequences of the invention under conditions where hybridization occurs between sequences of sufficient complementarity. Such duplexes may then be assessed for the presence of mismatched DNA. Mismatches may be due to the presence of a point mutation, insertion or deletion of nucleotide molecules. Detection of such mismatches may be performed using methods well known to those of skill in the art.

Nucleic acids encoding apoptosis modulators may also be introduced into host cells. In a preferred embodiment, HIV-1 infected T lymphoblastoid cells are provided which comprise an apoptosis modulator protein encoding nucleic acid such as SEQ ID NO: 1 or a variant thereof. Host cells contemplated for use include, but are not limited to, human, bacteria, yeast, insect and other animal cells. The nucleic acids may be operably linked to appropriate regulatory expression elements suitable for the particular host cell to be utilized. Methods for introducing nucleic acids into host cells are well known in the art. Such methods include, but are not limited to, transfection, transformation, calcium phosphate precipitation, electroporation and lipofection.

Host cells or extracts prepared therefrom containing apoptosis modulators may be used as screening tools to identify compounds which modulate their activity. Test compounds may be evaluated for their ability to inhibit HALP activity, for example, as assayed by activation of apoptotic pathways in and/or apoptosis of HIV-1 infected cells. Changes in apoptotic pathways may be measured using a variety of techniques, including, but not limited to those described in Example I. Modulation of apoptosis modulator activity in the context of a host cell may also be detected by changes in the level of apoptosis modulator gene expression (e.g., RNA or protein). Modulation of HALP activity, for example, may be assessed by measuring alterations in HALP binding activity or HALP biological activity in the presence of a test compound. Test compounds may also be assessed for the induction and/or suppression of expression of genes regulated by HALP.

The host cells described above may also be "primed" or "induced" to undergo apoptosis. Host cells induced to undergo apoptosis and extracts prepared thereof containing apoptosis modulators may be used as screening tools to identify compounds which alter protein activity. In vitro methods for inducing apoptosis are well known in the art and may comprise providing cells or tissues having cell surface receptors capable of mediating apoptosis such as a T cell receptor (TCR), a tumor necrosis factor (TNF) receptor, or a Fas receptor. Such methods comprise culturing cells under conditions (temperature, growth or culture medium and gas ($CO_2$)) and for an appropriate amount of time to attain exponential proliferation without density dependent constraints. Populations of cells undergoing exponential growth may be exposed to preliminary conditions necessary for apoptosis, an effective amount of an inducing agent, e.g., a TCR ligand, TNF, or a Fas ligand such as an anti-Fas antibody may be added to the culture. Anti-Fas antibodies and mitogens (ConA) capable of inducing apoptosis are well known to those of skill in the art (18, 19). Such cells are now "induced" to undergo apoptosis and may be cultured under suitable temperature and time conditions.

In one embodiment, cells are transfected with an effective amount of nucleic acid encoding an apoptosis modulators protein or a fragment thereof and the cells are cultured under suitable temperature and time conditions to inhibit apoptosis. The apoptosis modulator encoding nucleic acid may be transfected prior to, simultaneously with, or after, an apoptosis inducing agent. The cells are assayed for apoptotic activity using methods well known to those of skill in the art and described herein. In other embodiments, a drug or compound to be tested for the ability to alter apoptosis modulator activity may be added in varying concentrations at a time that is simultaneous with, prior to, or after the inducing agent. Those of skill in the art would recognize that such analyses must be performed with appropriate experimental controls.

Thus, the compositions and methods of the present invention provide a powerful in vitro drug screening bioassay of utility in the identification of drugs that are agonists or antagonists of apoptosis modulator function in host cells. Thus, one can screen for drugs capable of antagonizing or inhibiting apoptosis modulator activity that promote cellular apoptosis. One may also screen for drugs having similar or enhanced ability to prevent or inhibit apoptosis. One of skill in the art may determine when a drug is, for example, capable of enhancing HALP-mediated inhibition of apoptosis by noting a decrease in the number of morphological changes associated with apoptosis or a reduction in cell death. The in vitro method further provides an assay to determine if the methods and compositions of the invention are useful to treat a patient with a pathological condition or disease that has been linked to aberrant apoptotic cell death.

The availability of apoptosis modulator-encoding nucleic acids also enables the production of HIV-1 infected cells carrying part or all of an apoptosis modulator gene or mutated sequences thereof, in single or amplified copies.

The alterations to the apoptosis modulator genes envisioned herein include modifications, deletions, and substitutions. Such modifications, deletions or substitutions can result in an apoptosis modulator protein having altered characteristics or functions. As used herein, a "targeted gene" or "knock-out" is a DNA sequence introduced into host cells by way of human intervention, including but not limited to, the methods described herein. The targeted genes of the invention include DNA sequences which are designed to specifically alter apoptosis modulator regulation (e.g., inhibition or activation) of apoptosis in HIV-1 infected cells.

As described above, the apoptosis modulator-encoding nucleic acids are also used to advantage to produce large quantities of substantially pure proteins, or selected portions thereof.

B. Apoptosis Modulator Protein and Antibodies

Purified apoptosis modulator protein, or fragments thereof, may be used to produce polyclonal or monoclonal antibodies which also may serve as sensitive detection reagents for the presence and accumulation of HALP, for example, (or complexes containing HALP) in blood samples or cultured cells. Recombinant techniques enable expression of fusion proteins containing part or all of the apoptosis modulators of the invention. The full length protein or fragments of the protein may be used to advantage to generate an array of monoclonal antibodies specific for various epitopes of the protein, thereby providing even greater sensitivity for detection of the protein in HIV-1 infected cells.

Polyclonal or monoclonal antibodies immunologically specific for HALP, for example, may be used in a variety of assays designed to detect and quantitate the protein. Such assays include, but are not limited to: (1) flow cytometric analysis; (2) immunochemical localization of HALP in HIV-1 infected cells; and (3) immunoblot analysis (e.g., dot blot, Western blot) of extracts from leukocytes. Additionally, as described above, anti-HALP antibodies may be used for purification of HALP (e.g., affinity column purification, immunoprecipitation).

Antibodies immunologically specific for apoptosis modulators may also be used to inhibit the activity of apoptosis modulators in virus-infected (e.g., HIV-1) cells. Targeted delivery of anti-apoptosis modulator inhibitory antibodies to HIV-1 infected cells may be achieved by utilizing anti-gp120-antibody-studded liposomes comprising, for example, sfv-encoding antibodies immunologically specific for an apoptosis modulator. Methods for the production of such anti-gp120-antibody-studded liposomes and administration of targeted liposomes to patients have been previously described in Maulik et al. (20) and U.S. Pat. No. 5,709,879 (Barchfeld et al.); U.S. Pat. No. 5,935,937 (Smith); U.S. Pat. No. 5,981,279 (Weiss); and U.S. Pat. No. 6,025,193 (Weiss), the entire contents of which are incorporated herein by reference. In one aspect, sfv-encoding apoptosis modulator antibodies may be used which are specific for epitopes identified as essential for apoptosis modulator function and/or activity (e.g., anti-apoptotic activity). The binding of such sfv antibodies to HALP, for example, in HIV-1 infected cells mediates inhibition of HALP anti-apoptotic activity and thus, induces apoptosis of infected cells.

According to another aspect of the invention, methods of screening drugs for the treatment of HIV-1 infection which inhibit apoptosis modulator activity are provided. Inhibition of apoptosis modulator activity by gene transfer or by pharmacological means (e.g., small molecules which bind apoptosis modulators and thereby alter apoptosis modulator structure and/or function) would be expected to promote apoptotic activity of HIV-1 infected host cells.

The apoptosis modulator polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Upon expression of an apoptosis modulator polypeptide or fragment thereof, cells may be disrupted (e.g., by detergent or mechanical lysis) to produce a cellular lysate which may be affixed to a solid support for use in competitive binding assays. Such cells, either in viable or fixed form, may also be used for standard binding assays. One may determine, for example, formation of complexes between an apoptosis modulator polypeptide or fragment and the agent being tested, or examine the degree to which the formation of a complex between a apoptosis modulator polypeptide or fragment and a known ligand is interfered with by the agent being tested.

Another technique for drug screening provides high throughput screening for compounds having suitable binding affinity to an apoptosis modulator and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with an apoptosis modulator polypeptide and washed. Bound apoptosis modulator polypeptide is then detected by methods well known in the art.

Purified apoptosis modulators can be coated directly onto plates for use in the aforementioned drug screening techniques. However, non-neutralizing antibodies to the polypeptides can be used to capture antibodies to immobilize the apoptosis modulator polypeptide on the solid phase.

The present invention also contemplates the use of competitive drug screening assays in which neutralizing antibodies capable of specifically binding the apoptosis modulator polypeptide compete with a test compound for binding to the apoptosis modulator polypeptide or fragments thereof. In this manner, the antibodies can be used to detect the presence of any peptide which shares one or more antigenic determinants of the apoptosis modulator polypeptide.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson (21). In one approach, one first determines the three-dimensional structure of a protein of interest (e.g., apoptosis modulator) or, for example, of an apoptosis modulator containing complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (22). In addition, peptides (e.g., HALP polypeptide) may be analyzed by an alanine scan (23). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved apoptosis modulator activity or stability or which act as inhibitors, agonists, antagonists, etc. of such activity. By virtue of the availability of cloned apoptosis modulator sequences, sufficient amounts of the polypeptide may be made available to perform such analytical studies as x-ray crystallography. In addition, the knowledge of the protein sequences provided herein will guide those employing computer modeling techniques in place of, or in addition to x-ray crystallography.

V. Compositions Comprising Apotosis Modulator Nucleic Acid Molecules Proteins and Antibodies and Methods of Use Thereof Nucleic acid encoding apoptosis modulators, in either sense or antisense orientation, apoptosis modulator polypeptides and fragments thereof and antibodies thereto, and drugs or compounds identified by the methods of the present invention as having apoptosis modulating activity may be used to advantage as agents for the therapeutic treatment of an individual with a disease or condition which is linked to aberrant cellular apoptosis. Agents of the present invention may be administered using therapeutically effective administration protocols. Such protocols comprise suitable dose parameters and modes of administration that result in alleviation of symptoms related to a disease or condition which is linked to aberrant cellular apoptosis.

As used herein, the term "administering" for in vivo and ex vivo purposes refers to providing a subject with an amount of a nucleic acid molecule, polypeptide or antibody thereto sufficient to modulate apoptosis of a target cell. Methods of administering pharmaceutical compositions are well known to those of skill in the art and include, but are not limited to, microinjection, topical, oral, local, intravenous, subcutaneous, intramuscular, and parenteral administration. Administration may be effected continuously or intermittently throughout the course of treatment. Methods for determining the most effective means and dosage of administration are well known to those of skill in the art and will vary with the vector used for therapy, the nucleic acid used for therapy, the polypeptide used for therapy, the purpose of the therapy, the target cell being treated, and the subject being treated. Single or multiple administrations may be carried out with the dose level and pattern being selected by the attending physician. For example, the compositions may be administered to a subject prior to or after onset of a disease or condition that is associated with aberrant cellular apoptosis.

As used herein, a "therapeutically effective amount" of an agent or composition of the present invention is an amount sufficient to modulate apoptotic pathways in a patient with a disease or condition that is associated with aberrant cellular apoptosis.

In one embodiment, an expression construct comprising HALP-encoding nucleic acid in an antisense orientation, antisense HALP oligonucleotides, HALP siRNA molecules, or inhibitory antibodies immunologically specific for HALP for example, may be used to advantage as therapeutic agents to limit infection by an immunodeficiency virus (e.g., HIV-1) and/or prevent or treat AIDS in a patient. Therapeutically effective dose parameters and modes of administration may be determined using methods standard in the art. Such methods include, for example, determination of survival rates, side effects (i.e., toxicity) and progression or regression of disease. For example, a therapeutically effective dose and mode of administration for a formulation of the present invention may be determined by assessing response rates. Such response rates refer to the percentage of treated patients that responds with either partial or complete remission.

For the treatment of HIV-1 related diseases, a therapeutically effective dose of an agent or composition administered according to the present invention may depend on the viral load or cell tropism, as well as differences in levels of expression of immunodeficiency virus genes encoding apoptosis regulator proteins [e.g., HALP (disclosed herein), Vpr, Tat, Vif, Nef, Gag, and Vpu].

It will be obvious to one of skill in the art that the number of doses administered to a patient infected with an immunodeficiency virus is dependent upon the extent of the infection and the response of an individual to the treatment. For example, a patient with a high titer of HIV may require more doses than a patient with a lower titer. In some cases, however, a patient with a high titer of HIV may require fewer doses than a patient with a lower titer, if the former patient responds more favorably to the therapeutic composition than the latter patient. Thus, it is within the scope of the present invention that a suitable number of doses, as well as the time periods between administration, includes any number required to cause regression of a disease.

A therapeutic composition comprising agents of the present invention may also comprise a pharmaceutically acceptable carrier. As used herein, a "pharmaceutically acceptable carrier" refers to any substance suitable as a vehicle for delivering an agent of the present invention to a suitable in vitro or in vivo site of action. As such, carriers can act as a pharmaceutically acceptable excipient or formulation of a therapeutic composition containing agents. Preferred carriers are capable of maintaining agents of the present invention in a form that is capable of modulating (e.g., enhancing or inhibiting progression) of apoptosis of a cell. Examples of such carriers include, but are not limited to water, phosphate buffered saline, Ringer's solution, dextrose solution, serum-containing solutions, Hank's solution and other aqueous physiologically balanced solutions. Aqueous carriers may also contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances may also include preservatives, such as thimerosal, m- and o-cresol, formalin and benzol alcohol. Preferred auxiliary substances for aerosol delivery include surfactant substances non-toxic to a recipient, for example, esters or partial esters of fatty acids containing from about six to about twenty-two carbon atoms. Examples of esters include, caproic, octanoic, lauric, palmitic, stearic, linoleic, linolenic, olesteric, and oleic acids. Formulations of the present invention may be sterilized by conventional methods and/or lyophilized.

Useful carriers for agents of the present invention include any artificial or natural lipid-containing target molecule, preferably cells, cellular membranes, liposomes, and micelles. Preferably, formulations of the present invention are administered in the form of liposomes or micelles. Liposomes and micelles of the present invention are capable of delivering an agent from the extracellular space of a cell to the intracellular space of a cell. Agents of the present invention are combined with liposomes or micelles to provide a means for the delivery of a therapeutically effective amount of an agent to a cell such that the progression of apoptosis in such a cell is altered. Lipid-based carriers are particularly useful for embodiments of the present invention wherein a therapeutic composition comprises a nucleic acid molecule or antibody. Such delivery systems are known and have been successfully applied in the art and are discussed in Maulik et al. (20) and U.S. Pat. No. 5,709,879 (Barchfeld et al.); U.S. Pat. No. 5,935,937 (Smith); U.S. Pat. No. 5,981,279 (Weiss); and U.S. Pat. No. 6,025,193 (Weiss) which are incorporated by reference herein in their entirety.

In another embodiment, a "therapeutically effective amount" of a composition of the present invention may be administered to a patient to inhibit or at least partially arrest apoptosis and the accompanying pathology, such as is observed in a variety of disorders characterized by inordinate cellular apoptosis. Such diseases include but are not limited to acute and chronic inflammatory disease, leukemia, myocardial infarction, stroke, traumatic brain injury, neural and muscular degenerative diseases, aging, tumor induced-cachexia, hair loss, rheumatoid arthritis, and systemic lupus erythematosus.

The compositions may also be administered to subjects or individuals susceptible to or at risk of developing apoptosis-related disease to prevent pathological cell death. In one embodiment, the composition may be administered to a subject susceptible to a neural degenerative disease to maintain neuronal cell function and viability. In such embodiments, a "prophylactically effective amount" of the composition may be administered to maintain normal cellular viability and function.

It should be understood that by preventing or inhibiting unwanted cell death in a subject or individual, the compositions and methods of the invention also provide methods for treating, preventing and/or ameliorating the symptoms associated with a disease characterized by inordinate apoptosis of cells. Thus, the compositions and methods of the invention provide means to maintain cellular viability in patients with diseases associated with excessive and/or inappropriate apoptotic cell death.

VI. siRNA Molecules

As discussed hereinabove, small, interfering RNA (siRNA) molecules are typically double stranded RNA molecules (RNA is usually single stranded) which inhibit expression of its target mRNA (see, e.g. reference 27, particularly chapter 26). As used herein, the term siRNA may include what is sometimes referred to as short hairpin RNA (shRNA) molecules. Typically, shRNA molecules consist of short complementary sequences separated by a small loop sequence wherein one of the sequences is complimentary to the gene target. shRNA molecules are typically processed into an siRNA within the cell by endonucleases.

Chemically modified siRNA molecules may be employed in the instant invention. Non-limiting examples of such chemical modifications include, without limitation, phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. Preferably, the chemical modifications preserve the inhibition activity of the unmodified siRNA molecule in cells while, at the same time, increasing the serum stability of these compounds or other favorable property of the siRNA molecules. U.S. Patent Application Publication No. 20050032733, incorporated herein by reference, provides numerous suitable modifications of siRNA molecules.

Vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502-09). Preferably, RNA polymerase III promoters are employed. Preferable expression vectors for expressing the siRNA molecules of the invention are plasmids and viral vectors (see, e.g., Sui et al. (2002) PNAS 99:5515-5520; Xia et al. (2002) Nature Biotech. 20:1006-1010; Barton and Medzhitov (2002) PNAS 99:14943-14945; Brummelkamp et al. (2002) Science 296:550-553; Devroe and Silver (2002) BMC Biotechnol., 2(1):15; Tiscornia et al. (2003) PNAS, 100:1844-1848).

siRNA molecules targeting HALP may be administered alone or in combination with other siRNA molecules targeting other regions of HALP and/or at least one anti-HIV agents and/or at least one HIV vaccine. Anti-HIV agents include, without limitation: protease inhibitors (e.g., Indinavir, Ritonavir, Saqinavir, Nelfinavir, and Amprenavir), nucleoside reverse transcriptase inhibitors (e.g., Zidovudine (AZT), Didanosine, Zalcitabine, Lamivudine, Stavudine, and Abacavir), non-nucleoside reverse transcriptase inhibitors (e.g., Nevirapine, Delavirdine, and Efavirenz), integrase inhibitors, and fusion inhibitors.

Further details regarding the practice of this invention are set forth in the following examples, which are provided for illustrative purposes only and are in no way intended to limit the invention.

EXAMPLE I

Identification of HALP

In order to further elucidate the molecular mechanisms of HIV pathogenesis, PCR-select cDNA subtraction and differential screening were performed on T cells infected with HIV-1 IIIB isolates to identify cellular gene products involved in the regulation of apoptosis of HIV-1 infected cells. One such gene product, designated HALP, was identified as described below.

The following methods and protocols are provided to enable practice of the methods of Example I.
Cell Culture The CD4$^+$ T cell line CEM-SS was obtained from the repository of the NIH AIDS Research and Reference Reagent Program (from Dr. Peter L. Nara) and was maintained in RPMI 1640 medium (Gibco-BRL, Gaithersburg, Md.) supplemented with 10% fetal calf serum (FCS), 2 mM L-glutamine, 100 U/ml penicillin and 100 µg/ml streptomycin. The Hela-CD4-LTR-β-gal cell line was also obtained from the repository of the NIH AIDS Research and Reference Reagent Program (from Dr. Michael Emerman) and was maintained in DMEM (Gibco-BRL, Gaithersburg, Md.) supplemented with 10% FCS, 2 mM L-glutamine, 200 µg/ml G418 and 100 µg/ml hygromycin B.
Virus HIV-1 IIIB virus was obtained from the NIH AIDS Research and Reference Reagent Program and was passaged in CEM-SS cells. HIV-1 IIIB virus supernatant was harvested at days 7-9 post-infection, titered using Hela-CD4-LTR-β-gal cells and stored at −70° C.
HIV Infection Infection was achieved by incubating $3 \times 10^6$ CEM-SS cells at different multiplicities of infection (m.o.i). for 2 hours at 37° C. in 5% $CO_2$, followed by one RPMI 1640 wash. Mock infection was performed under the same conditions except that the supernatant was generated from uninfected cells. Cultured cells were counted and split every 2-3 days to maintain a concentration of $2 \times 10^5$ cells/ml.
P24 Expression and Detection of Apotosis Mock and HIV-1 IIIB infected CEM-SS cells ($1-2 \times 10^6$) were harvested and fixed in 1% paraformaldehyde for 30 minutes at room temperature. After fixation, samples were washed once in PBS. HIV-infected cells were identified by staining for expression of intracytoplasmic p24 gag. Cell were permeablized in 0.1% saponin (Sigma) and 10% FCS in PBS for 10 minutes at room temperature and then stained in the same buffer with 3 ml of PE-conjugated anti-p24 gag mAb(KC57-RD1, Coulter, Hialeah, Fla.) for 30 min at room temperature. All samples were also stained with isotype-matched control antibody (MsIgG1-RD1, Coulter). Four methods were utilized to identify apoptosis. First, the annexin V assay was performed, prior to cell fixation, according to the manufacturer's instructions (Caltag, Burlingame, Calif.). Second, the terminal deoxynucleotidyl transferase nick end-labelling (TUNEL) assay was used to detect ladder-like internucleosomal DNA fragmentation. In this assay, an APO-BRDU™ kit (Biosource International, Camarillo, Calif.) was used, as per the manufacturer's instruction manual. Third, after staining for TUNEL, cells with hypodiploid (sub G0/G1) DNA content were detected by staining with 10 µg/ml propidium iodide/RNase staining buffer (Biosource International, Camarillo, Calif.). Fourth, apoptotic cells exhibit morphological changes which may be readily detected flow cytometrically according to changes in forward- and side-scatter patterns. All samples were analyzed on a FACScan™ or FACSCalibur™ (Becton-Dickinson, San Jose, Calif.) flow cytometer. Data were collected and analyzed using Cellquest™ software (Becton-Dickinson).
Preparation of Poly(A)+ RNA CEM-SS cells were collected at day 7 and day 18 post HIV-1 IIIB infection and total cellular RNA was isolated using a RNeasy Mini Kit (QIAGEN, Valencia, Calif.) according to the manufacturer's instructions. Poly (A)+ RNA was prepared using Oligotex mRNA Kit (QIAGEN, Valencia, Calif.).
Suppression Subtractive Hybridization (SSH)

SSH was performed with the PCR-Select™ cDNA Subtraction Kit (Clontech, Palo Alto, Calif.) according to the manufacturer's protocol, except for the following modifications. In brief, 2 µg of day 7 and day 18 mRNA were used. Forward (day 7 subtracts day 18) and reverse (day 18 subtracts day 7) subtractions were performed. Primary PCR conditions were 30 cycles of 94° C., 30 seconds (s); 66° C., 30 s; and 72° C., 2 minutes (min) in a reaction volume of 25 µl, Secondary PCR conditions were 12 cycles of 94° C., 30 s; 68° C., 30 s; and 72° C., 2 min in a reaction volume of 25 µl. All PCR reactions were performed using a PTC-100™ Thermal Cycler (MJ Research, Watertown, Mass.). The subtracted PCR products were cloned directly into pT-Adv vector (Clontech, Palo Alto, Calif.).
Differential Screening Differential screening was performed using the PCR-Select™ Differential screening Kit (Clontech) according to the users' manual. Recombinant clones were randomly picked and cultured in 100 µl Luria broth (LB) in inidividual wells of 96-well plates. Such bacterial cultures were used directly in PCR amplifications. After amplification, 8 µl of the PCR product was denatured with 0.6 N NaOH. Two µl of each mixture was transferred to a Hybond™ N+ membrane (Amersham Pharmacia Biotech). Four identical blots were prepared for hybridization with different probes. The total secondary PCR products from the forward and reverse SSH and unsubtracted PCR products were used as probes. Probes were labeled in the presence of [$\gamma$-$^{32}$P]-dCTP (Dupont NEN, Boston, Mass.). The labeled probes were purified by QIAquick® Nucleotide Removal Kit (QIAGEN) and the specific activity of each probe was determined using a scintillation counter. Hybridizations were performed at 72° C. for 3 hr in ExpressHyb™ Hybridization Solution (Clontech) and an equal amount of each pair of probes (as determined by cpm) was used in hybridization reactions. After washing, membranes were exposed to x-ray film (Fuji, Tokyo, Japan) for varying lengths of time.
DNA Sequencing and Analysis Sequencing of cDNA inserts was accomplished in the Nucleic Acid Core Facility of The Children's Hospital of Philadelphia. Sequence homology searches were conducted using BLAST program against NCBI nonredundant database (www.ncbi.nlm.nih.gov/BLAST).

Northern Blotting

One μg messenger RNA (mRNA) was denatured and fractionated in 1% formaldehyde-agarose gels and transferred to Hybond™ N+ membrane using a vacuum blotter (Model 785, Bio-Rad) for 90 min. The membrane was illuminated using a UV-crosslinker (UV Stratalinker® 2400, Stratagene, La Jolla, Calif.) and stored at room temperature prior to hybridization reactions. The subtracted clones that were positive in differential screening analyses were further analyzed by probing of Northern blots. The blots were hybridized with cDNA probes labeled with [$\alpha$-$^{32}$P]-dCTP (RadPrime DNA Labeling System, Life Technology, Gaithersburg, Md.). The hybridization protocol was the same as above.

Results

Figure 2:
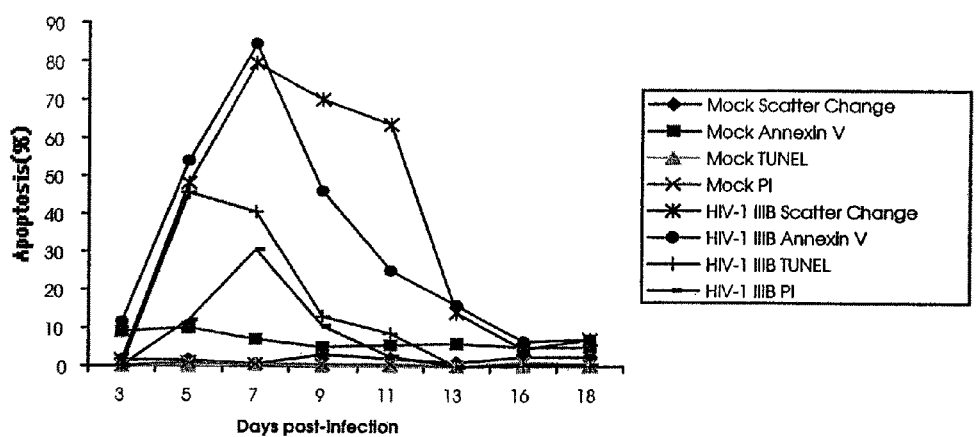
FIG. 2 shows a graph of apoptosis levels of CEM-SS cells mock-infected or infected with HIV-1 IIIB. Apoptosis was monitored flow cytometrically by analyses of light scatter change, annexin V staining, TUNEL, and staining for DNA content using propidium iodide.
Figure 3:
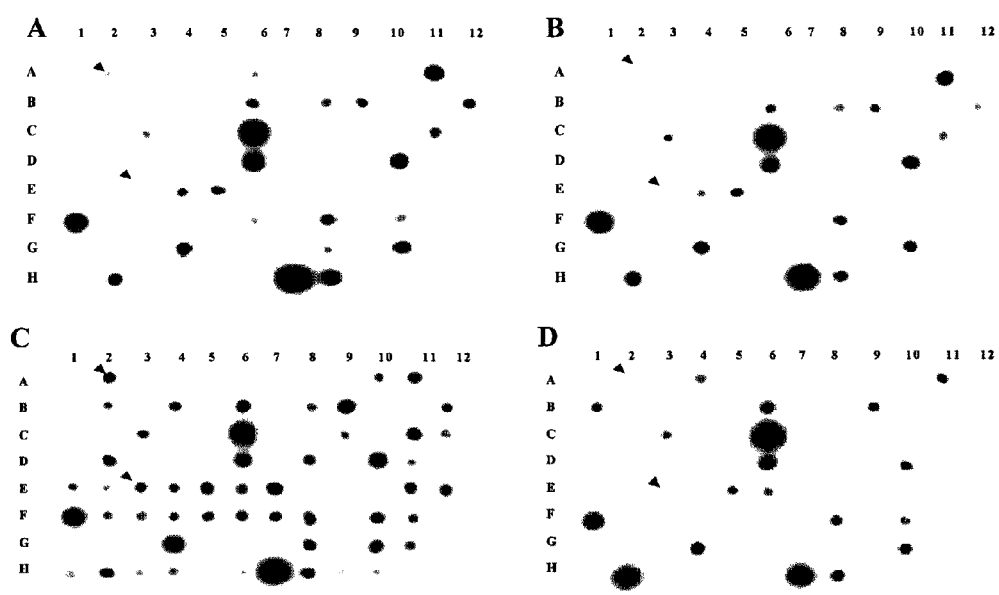
FIGS. 3A-3D show autoradiogram images from the differential screening of a subtracted day 18 cDNA library. The membranes were screened by hybridization with unsubtracted tester probe (FIG. 3A), unsubtracted driver probe (FIG. 3B), forward-subtracted probe (FIG. 3C) and reverse-subtracted probe (FIG. 3D). Hybridization signals were quantitated with a ratio of different intensities (with at least 3 indicating positive results). The arrows show the clones with positive results.

A. Dynamic Analysis of HIV-1 Infection and Apoptosis:

The human T lymphoblastoid cell line, CEM-SS, was mock-infected or infected with HIV-1 IIIB at a multiplicity of infection (m.o.i). of 0.05. Cell samples were collected at 2- or 3-day intervals post-infection and stained for p24 gag expression. Apoptosis of HIV-1 infected cells was monitored flow cytometrically by analyses of light scatter change and DNA content (using propidium iodide), and by fluorescent staining for annexin V, and TUNEL.

p24 gag expression in individual cells began to appear on day 3 post-infection (FIG. 1). The number of cells positive for p24 gag expression increased to 90% by day 5 and remained at high levels thereafter. Analyses of apoptosis showed that the CEM-SS cells underwent apoptosis at early stages of HIV-1 IIIB infection. The cell culture began to recover after day 9 and, by day 18, almost all of the infected cells were viable, even though they maintained the same level of infection (See FIG. 2). These results suggest that the HIV isolate, HIV-1 IIIB, mediates cell death at early stages of viral infection, but confers protection and/or resistance to apoptosis at later stages. These results may further suggest that only a sub-population of infected cells survive the early stages of infection (i.e., fail to undergo apoptosis), such that this sub-population of infected cells is essentially "selected for" on the basis of the cellular and viral interactions which conferred the enhanced survival properties. The development of such a sub-population of cells in vivo may provide a reservoir of viral particles, thus facilitating chronic HIV-1 IIIB infection.

B. PCR-Select cDNA Subtraction and Differential Screening:

The results of the dynamic analysis of HIV-1 IIIB infection and apoptosis further suggest that HIV encodes both pro-apoptotic and anti-apoptotic gene products (16), and that host cellular factors must also affect the outcome of HIV-1 infection (17). To identify the pro-apoptotic and anti-apoptotic gene products, cells were collected following HIV-1 IIIB infection, at the peak of apoptosis and at a later time point characterized by a stable cell population. mRNA was isolated from these "dying" and "viable" cell populations for use in double directional mRNA subtraction studies.

CEM-SS cells infected with HIV-1 IIIB were harvested at day 7 and day 18 post-infection. Two PCR-select cDNA subtractions were performed: a forward subtraction (day 7 minus day 18) and a reverse subtraction (day 18 minus day 7). The subtraction efficiency was evaluated by measuring residual levels of the housekeeping gene, GAPDH. After ensuring that GAPDH was fully removed from the subtracted pools, the subtracted cDNAs were cloned into TA cloning vectors and transformed into bacteria. The results of the differential screening and subtractive hybridization reactions are shown in FIGS. 3A-3D.

To identify pro-apoptotic gene products, 480 colonies containing cDNA inserts from the forward subtraction were picked at random and the inserts were re-amplified by PCR. The cDNA inserts were then arrayed on nylon membranes and differential screening was performed. See FIG. 15A.

To identify anti-apoptotic gene products, 384 colonies containing cDNA inserts from the reverse subtraction were picked randomly and the inserts were re-amplified by PCR. The cDNA inserts were then arrayed identically on four nylon membranes. Four probes (a day 18 probe, a day 7 probe, a forward-subtracted probe and a reverse-subtracted probe) were used to hybridize with the arrayed cDNA fragments to retain rare sequences and improve the sensitivity of the procedure. Hybridization signals were quantitated with a ratio of different intensities obtained by exposing the probed blots to film for different times. The differentially exposed film or autoradiograms were scanned and the density of the corresponding dots was measured utilizing Quantity One® Quantitation Software (BIO-RAD) using the same formats. The ODs of corresponding dots were compared and, if the ratio of the OD of corresponding spots was higher than 3, the corresponding clone was considered positive. For example, clone A; 18 unsubtracted probe, OD was 0.321; 7 unsubtracted probe, OD was 0.077; the ratio is 4.169, therefore clone A was considered positive. At least 3 positive ratios were required for scoring of a positive result.

Positive signals were detected in 80 out of 384 colonies derived from the reverse subtraction. See FIG. 15B. All of the positive clones were analyzed by DNA sequencing. Sequence homology searches and comparisons were performed using BLASTN on the National Center for Biotechnology Information web server. Of the 80 clone sequences, 46% (37) are identical to known genes, 28% (22) have full-length sequence in the database but are of unknown function, 20% (16) have sequences identical to sequences only in dbEST, one is a novel sequence, and two clones contain no insert. These genes are listed in FIG. 15 B.

C. Characterization of the HALP-Encoding Nucleic Acid Molecule

After database comparison, twenty cDNA fragments of interest were selected for Northern blot analysis. Of the twenty cDNA fragments, twelve have a known function, two are ESTs in the GenBank database, and six have full length sequence in the GenBank database, but have not been functionally characterized. Eighteen of the twenty clones were confirmed to be differentially expressed genes among mock control, day 7 and day 18 post-infection; 1 clone showed no signal; and 1 clone showed the same expression level in all three samples (control, day 7 and day 18).

FIG. 4 shows autoradiogram images of Northern blot analyses used to confirm the temporal expression pattern of clones identified by SSH and differential screening as being preferentially expressed at day 18. Specifically, the differential expression pattern of clones HALP, DF4, CC8, CD4, DF2, and DG1 over the course of HIV-1 infection is shown. Based on the correlation between their expression patterns and the apoptotic status of an HIV-1 infected cell population, clones HALP (SEQ ID NO: 1; FIG. 6), DF4 (SEQ ID NO: 13; FIG. 9), CC8 (SEQ ID NO: 12; FIG. 8), CD4 (SEQ ID NO: 15; FIG. 11), DF2 (SEQ ID NO: 14; FIG. 10), and DG1 (SEQ ID NO: 16; FIG. 12) clearly modulate apoptosis.

Figure 4A:
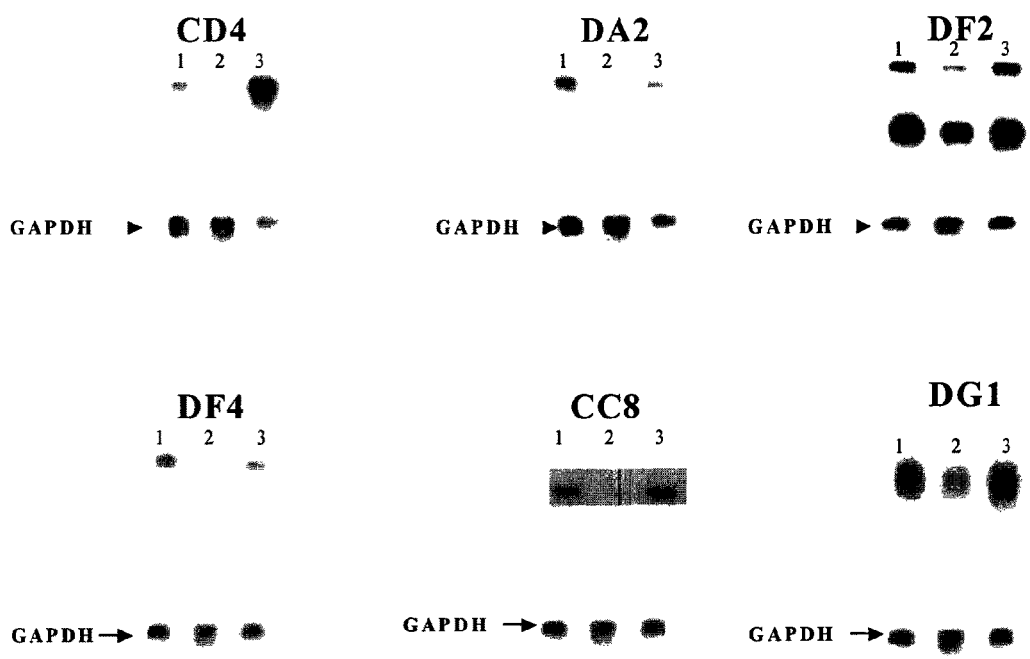
FIGS. 4A and 4B show the autoradiogram images of the Northern blot analyses used to confirm the putative differential expression of day 18 cDNA.

One of the differentially expressed gene products, designated HALP, was of particular interest because Northern blot analysis revealed that HALP expression decreased significantly at day 7 post-infection while expression levels recovered at day 18 post-infection (FIG. 4A). These results suggest that HALP has anti-apoptotic activity.

Figure 4B:
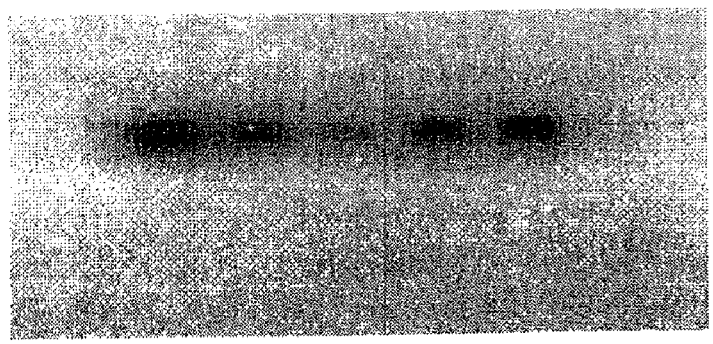

Dynamic analysis of HALP expression was performed to confirm these observations. After 3 days of HIV-1 IIIB infection, with p24 gag expression seen in 25% of the cells, HALP expression began to decrease (FIG. 4B, lane 2). Expression was almost completely lost at day 7 (lane 3), but began to increase at day 11 (lane 4), and returned to control levels at day 18 post-infection (lane 5).

The full length sequence of the HALP gene was found in the NCBI sequence database, although no known function was attributed to the sequence. The deduced amino acid sequence of HALP (SEQ ID NO: 2) was also searched in the NCBI sequence database using BLASTP. Significant homologies were seen with 7 "hypothetical" proteins, including 2 human proteins (GenBank accession numbers BAA91214 and CAB66603 (SEQ ID NOS: 2 and 3)), 2 mouse proteins (GenBank accession numbers BAB31006 and BAB24676 (SEQ ID NOS: 4 and 5)) and 3 fly proteins (GenBank accession numbers AAF59841, AAF50074, and AAF59840 (SEQ ID NOS: 6, 7 and 8)). Multiple sequence alignments of these sequences are shown in FIG. 5. These data suggest that HALP is a highly conserved gene product and, thus, plays an important role in cellular physiology.

Example II

Anti-Apoptotic HIV-1 Infected Cell Lines

Genes which are preferentially expressed on day 18, relative to day 7, post-infection with HIV-1 IIIB are candidate anti-apoptotic genes whose expression provides infected T cells with protection from apoptosis. Such genes may also play a role in the promotion of HIV transcription and/or replication. To confirm that genes identified by the methods of the present invention (e.g., HALP, CD4, DF2, DF4, CC8, and DG1) modulate HIV-1-induced apoptosis, HIV-1 infected cells and normal CEM-SS cells may be transduced with retroviral vectors expressing an identified gene product to establish stable cell lines that produce replication incompetent virus. Such cell lines provide useful reagents with which to monitor apoptosis of HIV-1 infected cells by methods described hereinabove and known to those skilled in the art. In one aspect, these transduction experiments may reveal the role of identified gene products in modulating apoptosis of HIV-1 infected cells. In another aspect, cell lines transduced with the above retroviral vectors provide a system of utility in screening agents (e.g., drugs or compounds) to identify those capable of modulating the activity of such a gene product.

Eukaryotic expression vectors may also be used to transiently transfect CEM-SS cells with HIV-1 LTR-Luc and HIV-1 ΔNRE-Luc reporter gene constructs (13). In such systems, retroviral expression vectors may be used to transfect packaging cell lines to produce replication incompetent virus. Control cells may be transduced with pseudotyped virus prepared from empty vector. The stable cell lines may be infected with HIV-1 IIIB, NL4-3 or various primary isolates in order to evaluate the apoptotic response of cells following viral infection. Identified gene products that modulate apoptosis of HIV infected cells may be investigated further utilizing functional and drug design analyses to provide novel reagents of utility in the treatment of HIV-1 infected patients.

Recent studies by Shiver et al. have reported promising results using replication-incompetent vaccine vectors to elicit effective anti-immunodeficiency virus immunity (24). Shriver and colleagues compared several vaccine vector delivery systems in a rhesus monkey model system to assess the ability of these different treatment modalities to elicit an immune response, The data demonstrated that the most effective immune responses were elicited by a replication-incompetent Ad5 vector encoding simian immunodeficiency (SIV) gag protein, used either alone or as a booster inoculation after priming with a DNA vector. Animals immunized with such AD5-SIV gag vectors exhibited the most pronounced attenuation of viral infection upon challenge with a pathogenic HIV-SIV hybrid virus. The immunizations did not, however, prevent subsequent infection. Moreover, a different study by Barouch et al. has revealed that recent successes using candidate AIDS vaccines to elicit potent virus-specific cytotoxic T lyumphocyte (CTL) responses may not provide lasting immunity (25). Barouch and colleagues demonstrated that viral escape from CTL recognition via mutation of a single viral nucleic acid sequence within an immunodominant Gag CTL epitope led to a burst of viral replication, clinical disease progression, and death from AIDS-related complications. In view of the profound difficulties encountered in the generation of vaccines for use in the prevention and/or treatment of HIV-1 infection, new research tools must be identified that surmount such challenges (26). The molecules of the present invention and methods of use thereof provide such novel research tools. The utility of these molecules as therapeutic agents and/or as targets of therapeutic intervention in the treatment of AIDS patients is particularly evident because such approaches are not negated by the ability of HIV-1 to mutate.

Example III

HALP Expression Modulates HIV-Induced Apoptosis

To confirm HALP expression modulates HIV-induced apoptosis, HALP was expressed in cells prior to HIV infection and apoptosis was monitored by morphological changes readily detected by flow cytometry. Specifically, CEM-SS cells, described hereinabove, were transfected with the ecdysone-inducible vector pVgRXR (Invitrogen, Carlsbad, Calif.), which encodes the ecdysone receptor subunits, using the FuGENE™ 6 transfection reagent (Roche, Indianapolis, Ind.) per the manufacturer's direction. Stably transfected cells were selected by growing the transfected CEM-SS cells in the presence of 300 μg/ml Zeocin™ (Invitrogen, Carlsbad, Calif.) beginning at 48 hours after transfection. The selection medium was subsequently changed every three days. The stably transfected cell line was named CEM-EcR.

pIND-GFP and PIND-GFP-HALP are derivatives of the pIND (Hygro) vector (Invitrogen, Carlsbad, Calif.). The pIND (Hygro) vector is an inducible expression plasmid which contains a hygromycin resistance gene and ecdysone response elements upstream of a minimal heat shock promoter and a multiple cloning site for the insertion of the gene of interest. pIND-GFP was created by amplifying a green fluorescent protein (GFP) template (provided by Dr. Warren Pear, University of Pennsylvania) by PCR with the following primers: 5' CGC GGA TCC GTG GCC ACA ACC ATG GTG AGC AAG 3' (SEQ ID NO: 17) and 5' CCG CTC GAG CGG AGC TAG CTT GCC AAA CCT ACA 3' (SEQ ID NO: 18). The PCR product was digested with BamH I and Xho I and inserted into a BamH I and Xho I digested pIND (Hygro) vector. The sequence of the GFP was confirmed by DNA sequencing.

pIND-GFP-HALP was synthesized by amplifying a HALP template by PCR with the following primers: 5' CGC GGA TCC GCG CTG TCC TCC TCA CCA TGG CTA 3' (SEQ ID NO: 19) and 5' CGC GGA TCC GCG GGC̄ GTA GTC GGG CAC GTC GTA GGG GTA TGA AGT TAA ACA CTC CTC AA 3' (SEQ ID NO: 20). The underlined g̅uanosine in SEQ ID NO: 19 was changed from a cytidine to correspond to the Kozak sequence. The underlined adenosine in SEQ ID NO: 20 was changed from a cytidine to change the stop codon to a codon for leucine. The italicized nucleotides in SEQ ID NO: 20 encode for the HA tag. The resultant PCR product was digested with BamH I and inserted into a BamH I digested pIND-GFP. The HALP sequence and orientation was confirmed by DNA sequencing. Notably, the coding region for HALP was placed 5' to the coding region for GFP. Therefore, the expression of GFP indicates that HALP was also expressed.

CEM-EcR cells were additionally transfected with either the pIND-GFP or pIND-GFP-HALP vector using the FuGENE™ 6 transfection reagent. Stably transfected cells were selected for by growing the transfected in cells in the presence of 100 µg/ml Zeocin™ and 100 µg/ml Hygromicin B (Roche, Mannheim, Germany) beginning at 48 hours post-transfection. The selection medium was subsequently changed every three days. Cells stably transfected with pIND-GFP were named CEM-EcR+GFP and cells stably transfected with pIND-GFP-HALP were named CEM-EcR+GFP-HALP. The cells used for the HIV infection experiments were further manipulated by sorting for only GFP positive cells on a FACStar™ Plus ACDU sorter (Cancer Center Flow Facility, University of Pennsylvania).

CEM-EcR, CEM-EcR+GFP, and CEM-EcR+GFP-HALP cells were challenged with HIV-1 IIIB virus as described hereinabove. At 3, 5, 7, and 10 days post-infection, infected cells were harvested, fixed, and stained for p24 as described hereinabove. The percentage of apoptotic cells was determined by changes in forward- and side-scatter patterns acquired by flow cytometry as described hereinabove. To monitor the apoptosis of only cells infected with HIV, only GFP and p24 positive cells were analyzed for forward- and side-scatter changes on a FACScan™ or FACSCalibur™ flow cytometer (Becton-Dickinson, San Jose, Calif.).

Figure 14A:
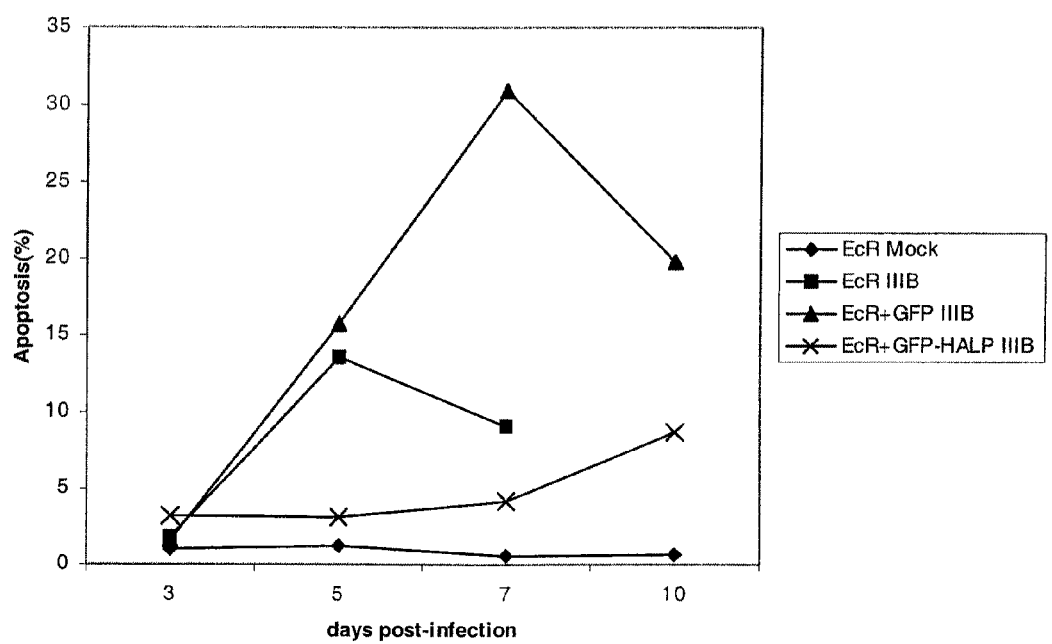
FIG. 14A is a graph of the apoptosis levels of both infected and uninfected cells over time. Apoptosis was monitored by flow cytometry by analysis of changes in forward and side scatter.
Figure 14B:
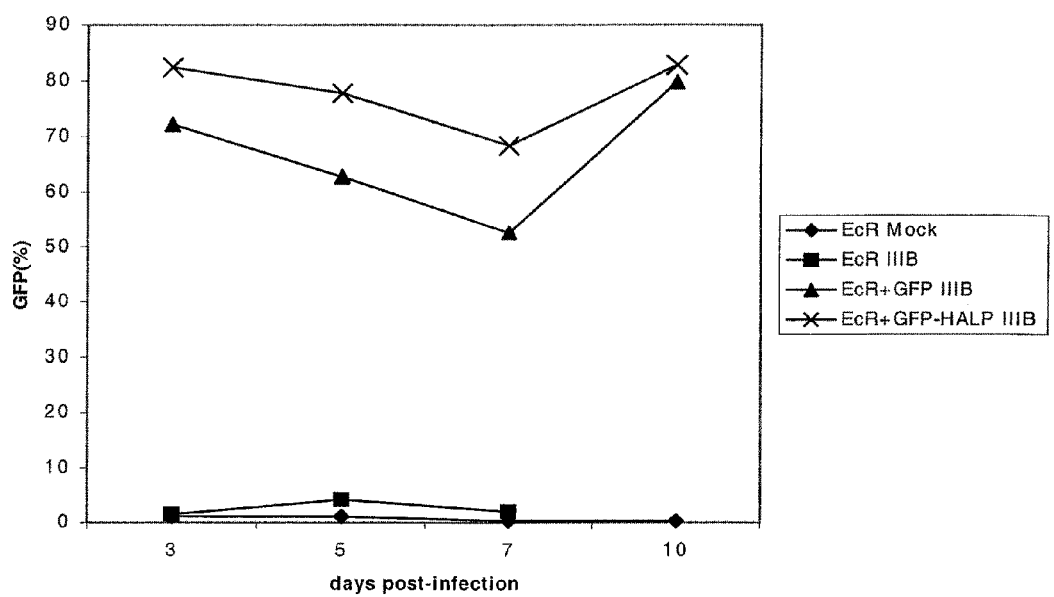
FIGS. 14 A through D are graphs of various analyses of mock infected CEM-EcR cells (EcR Mock), HIV IIIB infected CEM-EcR cells (EcR IIIB), HIV IIIB infected CEM-EcR+GFP cells (EcR+GFP IIIB), and HIV IIIB infected CEM-EcR+GFP-HALP cells (EcR+GFP-HALP IIIB).
In FIG. 14D, only infected cells that were positive for GFP and p24 expression were analyzed for changes in forward and side scatter.

As seen in FIG. 14A, CEM-EcR+GFP cells challenged with HIV IIIB are characteristically apoptotic by 7 days post-infection. Cultures expressing HALP in addition to GFP, however, had very low levels of apoptosis in comparison when challenged with HIV IIIB (see EcR+GFP-HALP). Importantly, expression from the minimal heat shock promoter of the pIND vectors was maintained as determined by monitoring of GFP (FIG. 14B). These results indicate that HALP expression modulates HIV-induced apoptosis.

Figure 14C:
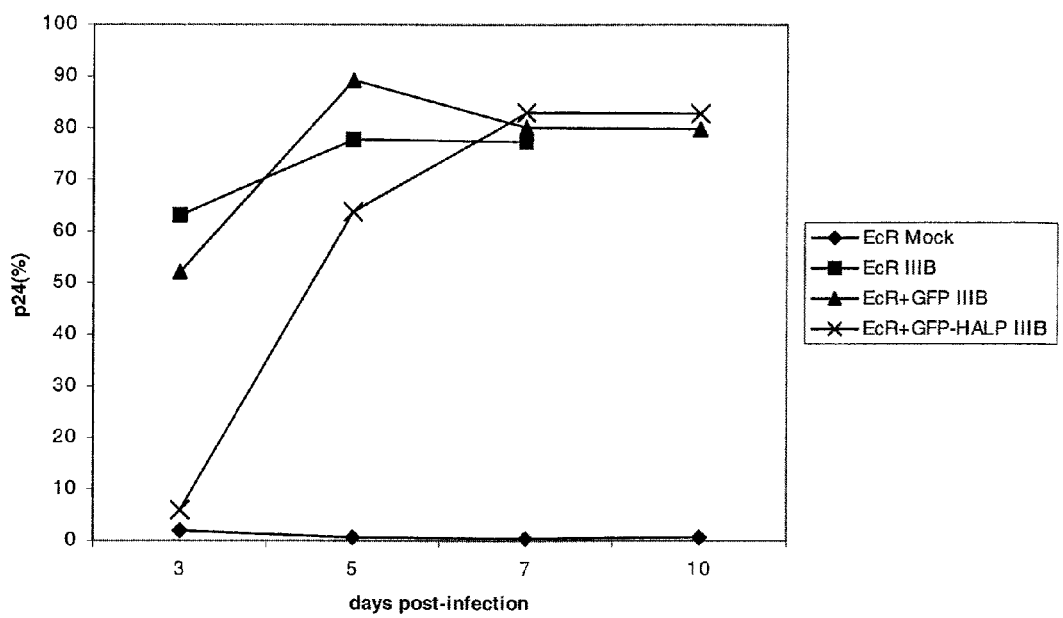
Figure 14D:
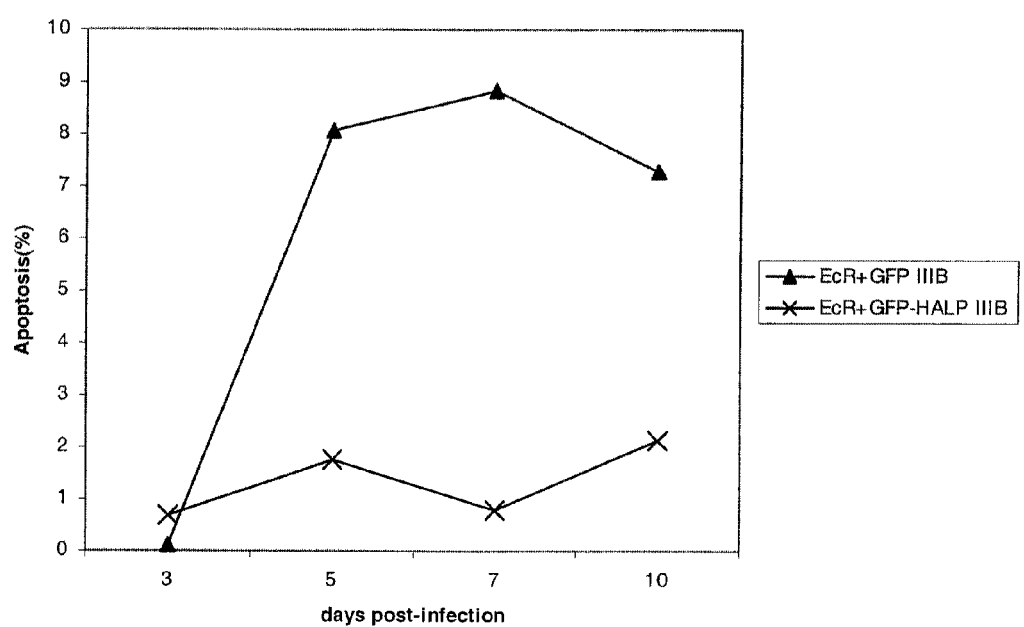

The spread of HIV IIIB on the CEM-EcR, CEM-EcR+GFP, and CEM-EcR+GFP-HALP cells was monitored by p24 staining (FIG. 14C). Notably, the spread of HIV IIIB on CEM-EcR+GFP-HALP cells was delayed at day 3 post-infection, but reached similar levels of spread by around day 5. To determine the effect of HALP expression specifically on infected cells, only cells found to be positive for GFP and p24 expression were analyzed by forward- and side-scatter (FIG. 14D). Again, HALP expressing cells demonstrate a significantly lower level of apoptosis compared to those expressing GFP alone. This data indicates that HIV-induced apoptosis is altered by HALP expression in infected cells.

Example IV

HALP siRNAs Modulate HIV-Induced Apoptosis

Figure 16:
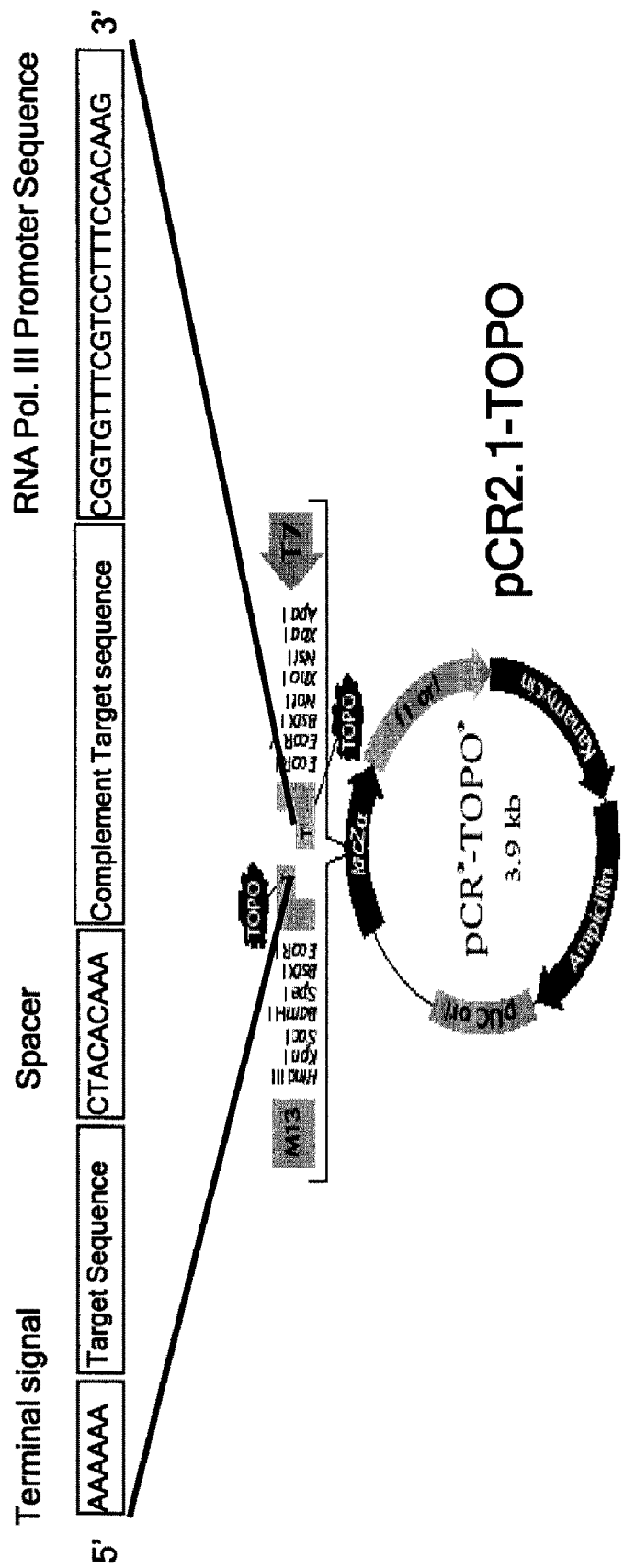
FIG. 16 is a schematic of an siRNA expression vector based on the pCR®2.1-TOPO® plasmid (Invitrogen; Carlsbad, Calif.). The RNA pol. III promoter sequence is SEQ ID NO: 25.

CEM-SS cells were transfected with different concentrations of a plasmid for the expression of a HALP siRNA. A schematic of the plasmid is shown in FIG. 16. Briefly, the vector allows for the expression of siRNA molecules within the cell by expressing an RNA molecule from the RNA polymerase III promoter sequence. The target sequence and the complement of the target sequence hybridize, thereby causing the expressed RNA molecule to "fold" back on itself as allowed by the generic spacer region. The now double-stranded RNA molecule is effective as an siRNA molecule within the cell. The sequences of the siRNA molecules tested are:

```
HALP siRNA sequences
HALP1:
GGA AGA CAC GGC TTA CCT GGA    (SEQ ID NO: 21)

HALP2:
GAT GCC TAG CCA GTT GGT AAG    (SEQ ID NO: 22)

HALP scrambled controls
HALP-SC1:
GCG ATT GCG CCA GAG ACA TAG    (SEQ ID NO: 23)

HALP-SC2:
GAT TCG GTG ATA CGA TCG CGA    (SEQ ID NO: 24)
```

Figure 17:
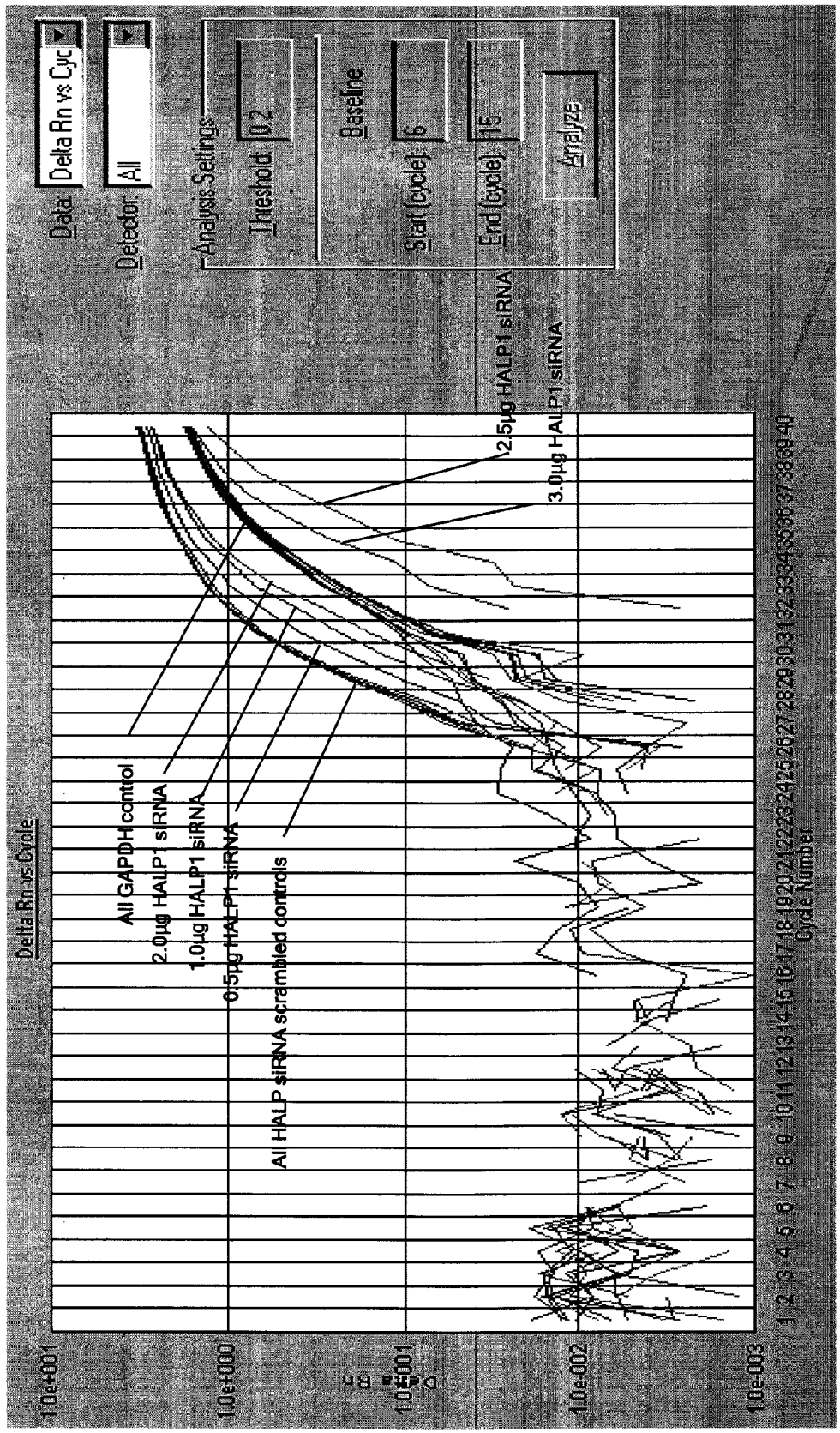
FIG. 17 is a graph of the results of a reverse transcriptase-real time PCR analysis of total RNA isolated from CEM-SS cells transfected with the indicated amounts of plasmids containing the indicated siRNAs.

Plasmids containing the above siRNA sequences were transfected into CEM-SS cells using a Nucleofector™ kit (Amaxa Biosystems; Gaithersburg, Md.). Seventy-two hours later, cells were collected and total RNAs were isolated. HALP expression levels were assayed using RT-real time PCR. As seen in FIG. 17, the silencing effects of HALP1 siRNA are linear between 0.5 and 2.5 µg of plasmid (psi-HALP1). At 2.5 µg, psiHALP1 inhibits endogenous HALP expression by more than 90%. Similar results were found for siRNA HALP2. No inhibition of HALP expression was found with either of the two scrambled controls.

siRNA molecules specific for HALP were also tested for their ability to modulate apoptosis in HIV-1 infected cells. Specifically, human primary CD4 T cells were isolated from healthy donors using the RosetteSep™ CD4+ T Cell Enrichment kit (StemCell Technologies; Vancouver, British Columbia, Canada). CD4 T-cells were activated using phytohemagglutinin (PHA; 1/100; Invitrogen). Forty-eight hours after activation, T-cells were transfected with either a plasmid for the expression of HALP siRNA or a plasmid for the expression of a random control siRNA. Twenty-four hours later, transfected cells were loaded on Ficoll-paque to separate dead from viable cells. Viable cells were subsequently infected with HIV-1 IIIB. For CEM-SS T cells, transfection procedures were performed 18 days after HIV-1 IIIB infection.

Figure 18:
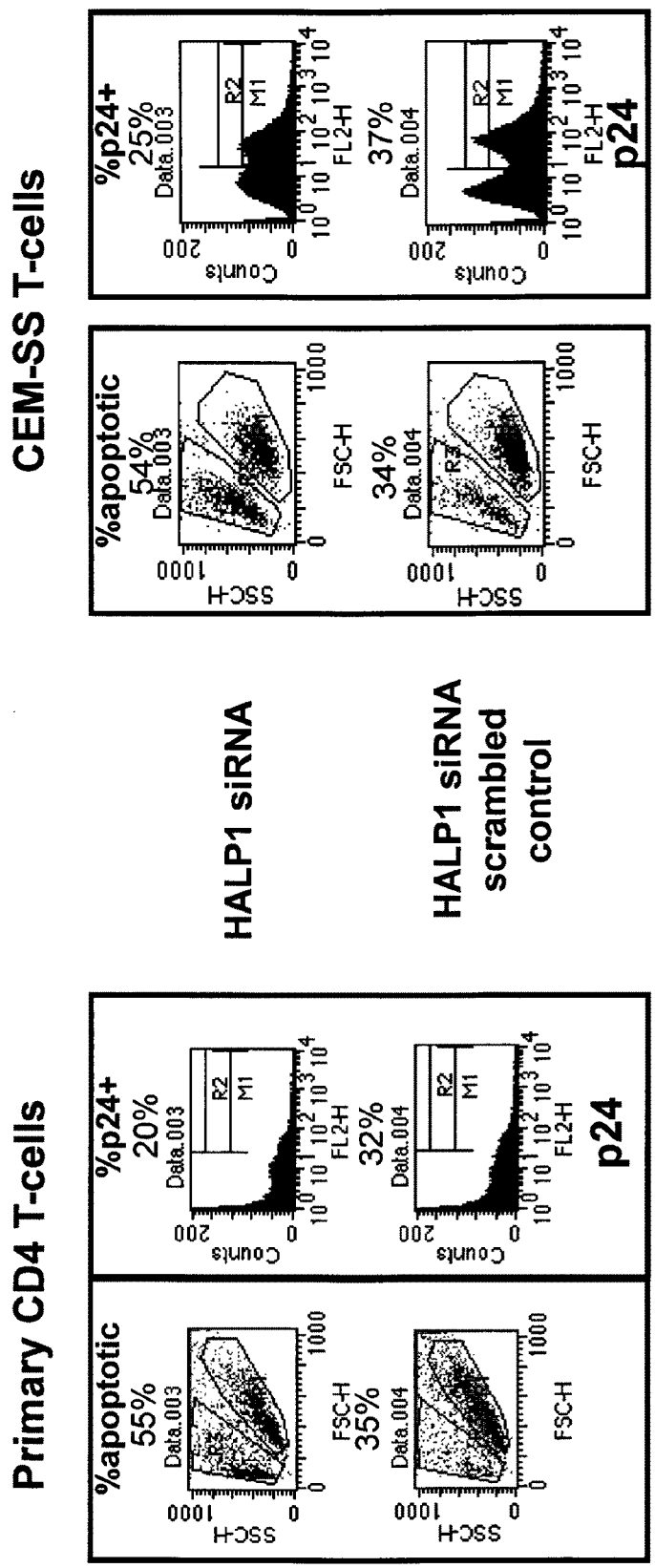
FIG. 18 contains graphs of flow cytometry experiments of either primary CD4 T cells or CEM-SS T cells infected with HIV-1 IIIB and transfected with either a plasmid for the expression of HALP1 siRNA or a plasmid for the expression of HALP1 siRNA scrambled control. The cells were analyzed for apoptosis by forward- and side-scatter analysis or analyzed for p24 gag.

Cells were collected every two or three days and stained with p24 antibody. Apoptosis was monitored by forward and side scatter change using flow cytometry. As seen in FIG. 18, the expression of the siRNA HALP1, but not the scrambled control, lead to increased apoptosis of infected T cells (compare percent apoptotic cells with HALP1 siRNA versus scrambled control) and a decrease in the number of infected cells (compare percent p24 positive cells with HALP1 siRNA versus scrambled control). The data in FIG. 18 represents primary T cells at 7 days post infection and CEM-SS T cells at 9 days.

Thus, inhibition of HALP activity by, for example, siRNA inhibition, leads to increased apoptosis of HIV-1 infected T cells and decreased infection levels in the remaining viable cells.

REFERENCES

1. Fauci A S. Host factors and the pathogenesis of HIV-induced disease. Nature 384:529-534, 1996.
2. McMichael A and Phillips R E. Escape of human immunodeficiency virus from immune control. Ann. Rev. Immunol. 15:271-296, 1997.
3. Pantaleo G, Fauci A S. Immunopathogensis of HIV infection, Ann. Rev. Microbiol. 50:825-854, 1996.
4. Deng H, Liu R, Ellmeier W, et al. Identification of the major co-receptor for primary isolates of HIV, Nature 381:661-666, 1996.
5. Liu R. Paxton W A, Choe S, et al. Homozygous defect in HIV-1 coreceptor accounts for resistance of some multiply-exposed individuals to HIV infection. Cell 86:367-377, 1996.
6. Murdoch C. CXCR4: chemokine receptor extraordinare. Immunol. Rev. 177:175-184, 2000.
7. Posada R, Pettoello-Mantovani M, Sieweke M, et al. Suppression of HIV type 1 replication by a dominant-negative Est-1 mutant. AIDS Res. and Hum. Retrovirus 18:1981-1989, 2000.
8. Nekhai S, Shukla R R, Fernandez A, et al. Cell cycle-dependent stimulation of the HIV-promoter by Tat-associated CAK activator. Virology 266:246-256, 2000.
9. Cron R Q, Bartz S R, Clause A, et al. NFAT1 enhances HIV-1 gene expression in primary human CD4 cells. Clin. Immunol. 94:179-191, 2000.
10. Kinoshita S, Chen B K, Kaneshima H, et al. Host control of HIV-1 parasitism in T cells by the nuclear factor of activated T cells. Cell 95:595-604, 1998.
11. Kinoshita S, Su L, Amano M, et al. The T cell activation factor NF-Atc positively regulates HIV-1 replication and gene expression in T cells. Immunity 6:235-244, 1997.
12. Finkel T H, Tudor-William G, Banda N K, et al, Apoptosis occurs predominantly in bystander cells and not in productively infected cells of HIV-infected lymph nodes. Nature Med. 1:129-134, 1995.
13. Perrin L and Telenti A. HIV treatment failure: Testing for HIV resistance in clinical practice. Science 280:1871-1873, 1998.
14. LaCasse R A, Follis K E, Trahey M, et al. Fusion-competent vaccines: broad neutralization of primary isolates of HIV. Science 283:357-362, 1999.
15. Nabel G J, Challenges and opportunities for development of an AIDS vaccine. Nature 410:1002-1007, 2001,
16. No name. Progress against HIV: The need for new treatments for AIDS is more urgent than ever, Nature Biotechnology 18 Supp:IT27-IT29, 2000,
17. Rowland-Jones S, Pinheiro S, Kaul R. New insights into host factors in HIV-1 pathogenesis. Cell 104:473-476, 2001.
18. Itoh N, Yonehara S, Ishii A, et al. The polypeptide encoded by the cDNA for human cell surface antigen Fas can mediate apoptosis. Cell 66:233-243, 1991.
19. Yonehara S, Ishii A, and Yonehara M. A cell-killing monoclonal antibody (anti-Fas) to a cell surface antigen co-downregulated with the receptor of tumor necrosis factor. J. Exp. Med. 169:1747-1756, 1989.
20. Maulik S and Patel S D. Molecular Biotechnology: Therapeutic Applications and Strategies. Wiley-Liss, Inc., 1997.
21. Hodgson J. Data-directed drug design. Biotechnology 9:19-21, 1991.
22. Erickson J, Neidhart D J, VanDrie J, et al. Design, activity, and 2.8 A crystal structure of a C2 symmetric inhibitor complexed to HIV-1 protease. Science 249:527-533, 1990.
23. Wells J A. Systematic mutational analyses of protein-protein interfaces. Meth. Enzym. 202:390-411, 1991.
24. Shiver J W, Fu T M, Chen L, et al. Replication-incompetent adenoviral vaccine vector elicits effective anti-immunodeficiency-virus immunity. Nature 415:331-335, 2002.
25. Barouch D H, Kunstman J, Kuroda M J, et al. Eventual AIDS vaccine failure in a rhesus monkey by viral escape from cytotoxic T lymphocytes, Nature 415:335-339, 2002.
26. Lifson J D and Martin M A. One step forwards, one step back. Nature 415:272-273, 2002.
27. Ausubel F M, Brent R, Kingston R E, Moore D D, Seidman J G, and Struhl K (1997) *Current Protocols in Molecular Biology*, John Wiley & Sons, New York.
28. Sambrook J, Fritsh E F, and Maniatis T (1989) *Molecular Cloning*, Cold Spring Harbor Laboratory Press, New York.
29. Harlow E and Lane D (1988) *Antibodies: A Laboratory Manual*, Cold Spring Harbor Laboratory Press, New York.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for decreasing the number of infected viable cells in a population of cells comprising contacting said population of cells with a therapeutically effective amount of at least one inhibitor of HIV-Associated Life Preserver (HALP) activity, thereby decreasing the number of infected viable cells in a population of cells, wherein said infected viable cells are infected with a retrovirus, wherein said inhibitor is a HALP antisense oligonucleotide or a HALP small interfering double stranded RNA (siRNA) molecule.

2. The method as claimed in claim 1, wherein said retrovirus is selected from the group consisting of human immunodeficiency virus 1 (HIV-1), human immunodeficiency virus 2 (HIV-2), simian immunodeficiency virus (SIV), and feline immunodeficiency virus (FIV).

3. The method as claimed in claim 2, wherein said retrovirus is human immunodeficiency virus 1 (HIV-1).

4. The method as claimed in claim 1, wherein said target cell is transformed with a recombinant expression vector for expressing the antisense oligonucleotide or the siRNA molecule.

5. The method of claim 1, wherein said inhibitor is administered to said target cell in combination with at least one anti-HIV agent.

6. The method of claim 5, wherein said anti-HIV agent is selected from the group consisting of protease inhibitors, nucleoside reverse transcriptase inhibitors, non-nucleoside reverse transcriptase inhibitors, integrase inhibitors, and fusion inhibitors.

7. The method of claim 1, wherein said contacting of said population of cells with said inhibitor of HALP activity induces apoptosis in said infected cells.

8. The method of claim 1, wherein the amino acid sequence of said HALP is SEQ ID NO: 2.

9. The method of claim 8, wherein each strand of said siRNA molecule is between about 12 and 30 nucleotides in length and the sequence of the sense strand of said siRNA molecule is homologous to a nucleic acid sequence encoding said HALP.

10. The method of claim 9, wherein each strand of said siRNA molecule is about 21 nucleotides.

11. The method of claim 10, wherein the GC content of said siRNA molecule is about 45% to about 55%.

12. The method of claim 1, wherein said nucleic acid sequence encoding HALP is SEQ ID NO: 1.

13. The method of claim 1, wherein said retrovirus is an immunodeficiency virus.

14. The method of claim 1, wherein said retrovirus is a lentivirus.

15. The method of claim 1, wherein said antisense molecule consists of 15 to 30 nucleotides and the sequence of the antisense molecule is complementary to a nucleic acid sequence encoding said HALP, and wherein each strand of said siRNA molecule is between about 12 and 30 nucleotides in length and the sequence of the sense strand of said siRNA molecule is homologous to a nucleic acid sequence encoding said HALP.

* * * * *

SEQUENCE LISTING

<160> NUMBER OF SEQ ID NOS: 25

<210> SEQ ID NO 1
<211> LENGTH: 714
<212> TYPE: DNA
<213> ORGANISM: Homo sapien

<400> SEQUENCE: 1

```
ctgtcctcac catgcctagc ctttgggacc gcttctcgtc gtcgtccacc tcctcttcgc      60
cctcgtcctt gccccgaact cccacccag atcggccgcc gcgctcagcc tgggggtcgg      120
cgacccggga ggagggtttt gaccgctcca cgagcctgga gagctcggac tgcgagtccc      180
tggacagcag caacagtggc ttcgggccgg aggaagacac ggcttacctg gatggggtgt      240
cgttgcccga cttcgagctg ctcagtgacc ctgaggatga acacttgtgt gccaacctga      300
tgcagctgct gcaggagagc ctggcccagg cgcggctggg ctctcgacgc cctgcgcgcc      360
```

| | | |
|---|---|---|
| tgctgatgcc tagccagttg gtaagccagg tgggcaaaga actactgcgc ctggcctaca | 420 | |
| gcgagccgtg cggcctgcgg ggggcgctgc tggacgtctg cgtggagcag ggcaagagct | 480 | |
| gccacagcgt gggccagctg cactcgacc ccagcctggt gcccaccttc cagctgaccc | 540 | |
| tcgtgctgcg cctggactca cgactctggc ccaagatcca ggggctgttt agctccgcca | 600 | |
| actctccctt cctccctggc ttcagccagt ccctgacgct gagcactggc ttccgagtca | 660 | |
| tcaagaagaa gctgtacagc tcggaacagc tgctcattga ggagtgttga actt | 714 | |

<210> SEQ ID NO 2
<211> LENGTH: 232
<212> TYPE: PRT
<213> ORGANISM: Homo sapien

<400> SEQUENCE: 2

Met Pro Ser Leu Trp Asp Arg Phe Ser Ser Ser Thr Ser Ser Ser
1               5                   10                  15
Pro Ser Ser Leu Pro Arg Thr Pro Thr Pro Asp Arg Pro Arg Ser
            20                  25                  30
Ala Trp Gly Ser Ala Thr Arg Glu Glu Gly Phe Asp Arg Ser Thr Ser
        35                  40                  45
Leu Glu Ser Ser Asp Cys Glu Ser Leu Asp Ser Asn Ser Gly Phe
    50                  55                  60
Gly Pro Glu Glu Asp Thr Ala Tyr Leu Asp Gly Val Ser Leu Pro Asp
65                  70                  75                  80
Phe Glu Leu Leu Ser Asp Pro Glu Asp Glu His Leu Cys Ala Asn Leu
                85                  90                  95
Met Gln Leu Leu Gln Glu Ser Leu Ala Gln Ala Arg Leu Gly Ser Arg
            100                 105                 110
Arg Pro Ala Arg Leu Leu Met Pro Ser Gln Leu Val Ser Gln Val Gly
        115                 120                 125
Lys Glu Leu Leu Arg Leu Ala Tyr Ser Glu Pro Cys Gly Leu Arg Gly
    130                 135                 140
Ala Leu Leu Asp Val Cys Val Glu Gln Gly Lys Ser Cys His Ser Val
145                 150                 155                 160
Gly Gln Leu Ala Leu Asp Pro Ser Leu Val Pro Thr Phe Gln Leu Thr
                165                 170                 175
Leu Val Leu Arg Leu Asp Ser Arg Leu Trp Pro Lys Ile Gln Gly Leu
            180                 185                 190
Phe Ser Ala Asn Ser Pro Phe Leu Pro Gly Phe Ser Gln Ser Leu
        195                 200                 205
Thr Leu Ser Thr Gly Phe Arg Val Ile Lys Lys Lys Leu Tyr Ser Ser
    210                 215                 220
Glu Gln Leu Leu Ile Glu Glu Cys
225                 230

<210> SEQ ID NO 3
<211> LENGTH: 232
<212> TYPE: PRT
<213> ORGANISM: Homo sapien

<400> SEQUENCE: 3

Met Pro Ser Leu Trp Asp Arg Phe Ser Ser Ser Thr Ser Ser Ser
1               5                   10                  15
Pro Ser Ser Leu Pro Arg Thr Pro Thr Pro Asp Arg Pro Arg Ser
            20                  25                  30

```
Ala Trp Gly Ser Ala Thr Arg Glu Glu Gly Phe Asp Arg Ser Thr Ser
            35                  40                  45

Leu Glu Ser Ser Asp Cys Glu Ser Leu Asp Ser Ser Asn Ser Gly Phe
 50                  55                  60

Gly Pro Glu Glu Asp Thr Ala Tyr Leu Asp Gly Val Ser Leu Pro Asp
 65                  70                  75                  80

Phe Glu Leu Leu Ser Asp Pro Glu Asp Glu His Leu Cys Ala Asn Leu
                 85                  90                  95

Met Gln Leu Leu Gln Glu Ser Leu Ala Gln Ala Arg Leu Gly Ser Arg
                100                 105                 110

Arg Pro Ala Arg Leu Leu Met Pro Ser Gln Leu Val Ser Gln Val Gly
            115                 120                 125

Lys Glu Leu Leu Arg Leu Ala Tyr Ser Glu Pro Cys Gly Leu Arg Gly
130                 135                 140

Ala Leu Leu Asp Val Cys Val Glu Gln Gly Lys Ser Cys His Ser Val
145                 150                 155                 160

Gly Gln Leu Ala Leu Asp Pro Ser Leu Val Pro Thr Phe Gln Leu Thr
                165                 170                 175

Leu Val Leu Arg Leu Asp Ser Arg Leu Trp Pro Lys Ile Gln Gly Leu
                180                 185                 190

Phe Ser Ser Ala Asn Ser Pro Phe Leu Pro Gly Phe Ser Gln Ser Leu
                195                 200                 205

Thr Leu Ser Thr Gly Phe Arg Val Ile Lys Lys Lys Leu Tyr Ser Ser
210                 215                 220

Glu Gln Leu Pro Ile Glu Glu Cys
225                 230

<210> SEQ ID NO 4
<211> LENGTH: 229
<212> TYPE: PRT
<213> ORGANISM: Mus musculus

<400> SEQUENCE: 4

Met Pro Ser Leu Trp Asp Arg Phe Ser Ser Ser Ser Ser Ser Ser Ser
 1               5                  10                  15

Ser Ser Arg Thr Pro Ala Ala Asp Arg Pro Pro Arg Ser Ala Trp Gly
             20                  25                  30

Ser Ala Ala Arg Glu Glu Gly Leu Asp Arg Cys Ala Ser Leu Glu Ser
            35                  40                  45

Ser Asp Cys Glu Ser Leu Asp Ser Ser Asn Ser Gly Phe Gly Pro Glu
 50                  55                  60

Glu Asp Ser Ser Tyr Leu Asp Gly Val Ser Leu Pro Asp Phe Glu Leu
 65                  70                  75                  80

Leu Ser Asp Pro Glu Asp Glu His Leu Cys Ala Asn Leu Met Gln Leu
                 85                  90                  95

Leu Gln Glu Ser Leu Ser Gln Ala Arg Leu Gly Ser Arg Arg Pro Ala
                100                 105                 110

Arg Leu Leu Met Pro Ser Gln Leu Val Ser Gln Val Gly Lys Glu Leu
            115                 120                 125

Leu Arg Leu Ala Tyr Ser Glu Pro Cys Gly Leu Arg Gly Ala Leu Leu
130                 135                 140

Asp Val Cys Val Glu Gln Gly Lys Ser Cys His Ser Val Ala Gln Leu
145                 150                 155                 160

Ala Leu Asp Pro Ser Leu Val Pro Thr Phe Gln Leu Thr Leu Val Leu
                165                 170                 175
```

```
Arg Leu Asp Ser Arg Leu Trp Pro Lys Ile Gln Gly Leu Leu Ser Ser
            180                 185                 190

Ala Asn Ser Ser Leu Val Pro Gly Tyr Ser Gln Ser Leu Thr Leu Ser
            195                 200                 205

Thr Gly Phe Arg Val Ile Lys Lys Leu Tyr Ser Ser Glu Gln Leu
        210                 215                 220

Leu Ile Glu Glu Cys
225

<210> SEQ ID NO 5
<211> LENGTH: 193
<212> TYPE: PRT
<213> ORGANISM: Mus musculus

<400> SEQUENCE: 5

Met Val Ala Thr Gly Ser Leu Ser Ser Lys Asn Pro Ala Ser Ile Ser
1               5                   10                  15

Glu Leu Leu Asp Gly Gly Tyr His Pro Gly Ser Leu Leu Ser Asp Phe
            20                  25                  30

Asp Tyr Trp Asp Tyr Val Val Pro Glu Pro Asn Leu Asn Glu Val Val
        35                  40                  45

Phe Glu Glu Thr Thr Cys Gln Asn Leu Val Lys Met Leu Glu Asn Cys
50                  55                  60

Leu Ser Arg Ser Lys Gln Thr Lys Leu Gly Cys Ser Lys Val Leu Val
65                  70                  75                  80

Pro Glu Lys Leu Thr Gln Arg Ile Ala Gln Asp Val Leu Arg Leu Ser
                85                  90                  95

Ser Thr Glu Pro Cys Gly Leu Arg Gly Cys Val Met His Val Asn Leu
            100                 105                 110

Glu Ile Glu Asn Val Cys Lys Lys Leu Asp Arg Ile Val Cys Asp Ala
        115                 120                 125

Ser Val Val Pro Thr Phe Glu Leu Thr Leu Val Phe Lys Gln Glu Ser
    130                 135                 140

Cys Pro Trp Thr Ser Leu Lys Asp Phe Phe Phe Ser Arg Gly Arg Phe
145                 150                 155                 160

Ser Ser Gly Leu Lys Arg Thr Leu Ile Leu Ser Ser Gly Tyr Arg Leu
                165                 170                 175

Val Lys Lys Lys Leu Tyr Ser Leu Ile Gly Thr Thr Val Ile Glu Glu
            180                 185                 190

Cys

<210> SEQ ID NO 6
<211> LENGTH: 280
<212> TYPE: PRT
<213> ORGANISM: Drosophila melanogaster

<400> SEQUENCE: 6

Met Lys Met Asp Val Ile Ala Arg Glu Gln Ile Ile Tyr Gly Ser Leu
1               5                   10                  15

Gln Gly Ser Asn Lys Asn Lys Asp Trp Thr Ser Arg Leu Pro Pro Pro
            20                  25                  30

Ser Ala Tyr Thr Leu Asp Leu Met Ser Lys Lys Ala Lys Thr Thr Thr
        35                  40                  45

Gly Gly Ser Ser Asn Gly Ser Asn Ala Thr Ala Thr Ser Thr Thr Thr
    50                  55                  60

Ser Thr Ser Ser Ser Ile Lys His Lys Gln Pro Ala Gly Ser Ser Asn
65                  70                  75                  80
```

```
Asn Asn Val Gly Gln Ser Gln Ser Lys Lys Thr Lys Pro Ser Gly Ser
             85                  90                  95

Tyr Asn Ser Asn Ser Asn Tyr Tyr Tyr Ala Ala Asp Glu Glu Glu
            100                 105                 110

Gly Gly Ser Ala Asp Tyr Ala Leu Ser Asn Tyr Asp Lys Lys Ala Val
            115                 120                 125

Glu Glu Leu Ser Leu Arg Leu Leu Asp Glu Leu Arg Ala Ala Lys Ser
130                 135                 140

Arg His Leu Thr Cys Thr Glu Val Ser Leu Pro Cys Asp Leu Thr Pro
145                 150                 155                 160

Ser Val Ala Arg Glu Ile Ile Arg Val Ser Glu Lys Glu Pro Arg Gly
                165                 170                 175

Ile Arg Gly Cys Thr Ile Tyr Ile Glu Phe Glu Asp Glu Pro Lys Asn
            180                 185                 190

Ser Arg Arg Ile Ala Ser Ile Lys Val Asp Pro Asp Thr Val Ser Thr
            195                 200                 205

Phe Glu Val Tyr Leu Thr Leu Arg Gln Asp His Arg Gly Trp Thr Ser
210                 215                 220

Leu Leu Pro Gln Phe Met Lys Ser Leu Ala Arg Thr Ile Thr Ile Ser
225                 230                 235                 240

Pro Glu Tyr Thr Ile Thr Lys Asn Lys Leu Tyr Ser Ala Asp Gly Leu
                245                 250                 255

Gly Ala Arg Arg Ser Tyr Ser Phe Gly Ser His Ala His Arg Pro Ser
            260                 265                 270

Ala Ala Ile Ala Thr Pro Thr Asn
            275                 280

<210> SEQ ID NO 7
<211> LENGTH: 280
<212> TYPE: PRT
<213> ORGANISM: Drosophila melanogaster

<400> SEQUENCE: 7

Met Lys Met Asp Val Ile Ala Arg Glu Gln Ile Ile Tyr Gly Ser Leu
  1               5                  10                  15

Gln Gly Ser Asn Lys Asn Lys Asp Trp Thr Ser Arg Leu Pro Pro Pro
             20                  25                  30

Ser Ala Tyr Thr Leu Asp Leu Met Ser Lys Lys Ala Lys Thr Thr Thr
            35                  40                  45

Gly Gly Ser Ser Asn Gly Ser Asn Ala Thr Ala Thr Ser Thr Thr Thr
        50                  55                  60

Ser Thr Ser Ser Ser Ile Lys His Lys Gln Pro Ala Gly Ser Ser Asn
 65                  70                  75                  80

Asn Asn Val Gly Gln Ser Gln Ser Lys Lys Thr Lys Pro Ser Gly Ser
             85                  90                  95

Tyr Asn Ser Asn Ser Asn Tyr Tyr Tyr Ala Ala Asp Glu Glu Glu
            100                 105                 110

Gly Gly Ser Ala Asp Tyr Ala Leu Ser Asn Tyr Asp Lys Lys Ala Val
            115                 120                 125

Glu Glu Leu Ser Leu Arg Leu Leu Asp Glu Leu Arg Ala Ala Lys Ser
130                 135                 140

Arg His Leu Thr Cys Thr Glu Val Ser Leu Pro Cys Asp Leu Thr Pro
145                 150                 155                 160

Ser Val Ala Arg Glu Ile Ile Arg Val Ser Glu Lys Glu Pro Arg Gly
                165                 170                 175
```

```
Ile Arg Gly Cys Thr Ile Tyr Ile Glu Phe Glu Asp Glu Pro Lys Asn
            180                 185                 190

Ser Arg Arg Ile Ala Ser Ile Lys Val Asp Ser Asp Thr Val Ser Thr
            195                 200                 205

Phe Glu Val Tyr Leu Thr Leu Arg Gln Asp His Arg Gly Trp Thr Ser
210                 215                 220

Leu Leu Pro Gln Phe Met Lys Ser Leu Ala Arg Thr Ile Thr Ile Ser
225                 230                 235                 240

Pro Glu Tyr Thr Ile Thr Lys Asn Lys Leu Tyr Ser Ala Asp Gly Leu
                245                 250                 255

Gly Ala Arg Arg Ser Tyr Ser Phe Gly Ser His Ala His Arg Pro Ser
            260                 265                 270

Ala Ala Ile Ala Thr Pro Thr Asn
            275                 280

<210> SEQ ID NO 8
<211> LENGTH: 299
<212> TYPE: PRT
<213> ORGANISM: Drosophila melanogaster

<400> SEQUENCE: 8

Met Lys Met Glu Val Leu Ser Val Gln Asn His Ile Gln Gly Lys Phe
1               5                   10                  15

Gly Val Asn Lys Ile Lys Asp Trp Gln Ala Ser Thr Ala Pro Leu Glu
            20                  25                  30

Glu Glu Glu Glu Leu Thr Ala Gly Val Asn Gly Asn Thr Ala Ala Gly
        35                  40                  45

Glu Gly Ile Leu Asp Val Asp Val Val Asp Gly His Pro Ala Ser Val
    50                  55                  60

Leu His Met Arg Gln His Gln Ala Leu Asn Thr Arg Pro Ser Ala Thr
65                  70                  75                  80

Pro Pro Ser Ala Gly Gly Gly Pro Leu Ala Gly Gly Gly Ser Val
                85                  90                  95

Gly Met Thr Thr Pro Lys Gln Ala Thr Ser Pro Val Ala Ala Ala Ser
            100                 105                 110

Phe Glu Ala Pro Leu Ser Gly Gly Ser Ala Ala Ala Tyr His His Ala
        115                 120                 125

Tyr Met Thr Asn Val Leu Ser Ser Thr Ala Gln Gln His His Pro Leu
    130                 135                 140

Pro Ala Ser Pro Leu Gln Ser Thr Ala Gly Ala Arg Phe Gly Ala Ala
145                 150                 155                 160

Asp Asn Leu Asp Asp Val Ser Ala Ser Ala Val Arg Glu Leu Ser Gln
                165                 170                 175

Gln Leu Gln Ala Gln Leu Arg Asp Ala Lys Arg Arg His Leu Ala Cys
            180                 185                 190

Thr Glu Val Thr Leu Pro Asn Asp Leu Thr Gln Arg Ile Ala Ala Glu
        195                 200                 205

Ile Ile Arg Met Ser Glu Arg Glu Pro Cys Gly Glu Arg Ala Cys Thr
    210                 215                 220

Leu Phe Ile Glu Phe Glu Ser Glu Pro Asn Lys Val Lys Arg Ile Ala
225                 230                 235                 240

Tyr Phe Lys Val Asp Pro Asp Thr Val Ser Ile Phe Glu Leu Tyr Leu
                245                 250                 255

Thr Leu Arg Gln Asp Lys Ser Gly Trp Ser Ser Leu Val Pro Gln Phe
            260                 265                 270
```

```
Ile Lys Asn Leu Thr Arg Ser Asn Thr Ile Asn Ile Ser Pro Asp Phe
        275                 280                 285
Thr Leu Thr Lys Lys Lys Leu Tyr Ser Ser Glu
        290                 295
```

<210> SEQ ID NO 9
<211> LENGTH: 415
<212> TYPE: DNA
<213> ORGANISM: Homo sapien

<400> SEQUENCE: 9

```
agcgtggtcg ccgccgaggt accttattat ttttgttact gacagttaac agtggtgtga      60
catccagaga gcagctgggc tgctcccgcc ccagcccggc ccagggtgaa ggaagaggca     120
cgtgctcctc agagcagccg agggaggggg ggaggtcgga ggtcgtggag gtggtttgtg     180
tatcttactg gtctgaaggg accaagtgtg tttgttgttt gttttgtatc ttgttttcct     240
gatcggagca tcactactga cctgttgtag gcagctatct tacagacgca tgaatgtaag     300
agtaggaagg ggtgggtgtc agggatcact tgggatcttt gacacttgaa aaattacacc     360
tggcagctgc gtttaagcct tcccccatcg tgtacctgcc cgggcggccg ctcga          415
```

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10

```
ctgtcctcac catgccta                                                    18
```

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11

```
tgaagttcaa cactcctcaa                                                  20
```

<210> SEQ ID NO 12
<211> LENGTH: 696
<212> TYPE: DNA
<213> ORGANISM: Homo sapien

<400> SEQUENCE: 12

```
aggtacccat gctcacacac acacacttcc agttttatac aaatttttt aaaggaaaga       60
aaccaaccca agtattgca tttgaggtga cactccctga agaattttat acagaggtaa      120
tatactgttt ggcacagctg aaggtttttt tattctttct tttttaaag tgagcccatg      180
atttggtgtc tttcccagat tatccccttt gcgacaacac aagcaaaaat atttacaaag    240
gtaaggcata gtcaaactac ataaagagaa aaaatcatga ggaaaataca tgaaaaagac     300
taaagacttc gccataacaa ggtcttagtg ataatagtgt ccgtaaagat gtcatcagaa     360
ttggtaaagt caagcatgct gcaaatatac cctttggatt agaaaagagc acaatttcct    420
tttttgttt tgttctgttt taagaagtgg catactgctc tttctcccctt tggataattt     480
cttttaagcc catcaaagga aaaaacaaac acaattcaaa caaacactgt caagtgattc     540
aagatcaaat atttacaata atcaaatgga gtatcagatt ttttttccaa actgatacca    600
```

```
caaatacaga gctgaaatct ctctttggct cctctatatg caaaattgaa ttagtcttca    660
ttgaagacaa ttatatagtc agttccagat gcaaaa                              696

<210> SEQ ID NO 13
<211> LENGTH: 509
<212> TYPE: DNA
<213> ORGANISM: Homo sapien

<400> SEQUENCE: 13
ttagcgtggt cgcggccgag gtacggtcgt tgcccatggt gattaaagtg tggttatggg     60
caggaagaca gactgtgtaa aaaaggaatg acatcctggc tcctcatctt cttcatcagc    120
aactaccata accagtttgc gagtcaaatg gcatttccta acggcaggca tggcggcccc    180
tgaaagacaa cagctcccct tctgcttcgg acaccactca aacatttaga cgcagctcta    240
tcccttttcc tagctagaga aggtgatgcc ttcttccatt actcagagat gttgagacgt    300
tttcagaatt tcttgttgaa atgaaaaaca tcaagataaa ggacgccttt caggcattag    360
ctaaacttcc acttcataac tttcggcgag acatggtgag cctcctggtg tagagttctt    420
ttgtctttgt atggaatgac ttttttgctgt gatggttttg aatgttgggt ttctgctgtc    480
tgcttagtac ctgcccgggc ggccgctcg                                      509

<210> SEQ ID NO 14
<211> LENGTH: 450
<212> TYPE: DNA
<213> ORGANISM: Homo sapien
<220> FEATURE:
<221> NAME/KEY: misc_feature
<222> LOCATION: (0)...(0)
<223> OTHER INFORMATION: n = A, C, G or T

<400> SEQUENCE: 14
gcggccgagg tgacggagag gaaacctgcg ccctggcctc tcactccggg agctcaggct     60
ccaagtcggg aggcgacaag atgttctccc tcaagaagtg gaacgcggtg gccatgtgga    120
gctgggacgt ggagtgcgat acgtgcgcca tctgcaggt ccagtggtct ggggagaatg    180
taatcattcc ttccacaact gctgcatgtc cctgtgggtg aaacagaaca atcgntgccc    240
tctctgccag caggactggg tggtccaaaa aatcggcaaa tgagagtggt tagaaggctt    300
cttancgcag ttgttcagag ccctggtgga tcttgtaatc cagtgcccta caaaggctag    360
aacactacag ggtcgtcttc gtcctcatcg ccactctcct nanggatggc gacctgcccg    420
ggcggccgnt cgaaagccga attccagcac                                     450

<210> SEQ ID NO 15
<211> LENGTH: 471
<212> TYPE: DNA
<213> ORGANISM: Homo sapien
<220> FEATURE:
<221> NAME/KEY: misc_feature
<222> LOCATION: (0)...(0)
<223> OTHER INFORMATION: n = A, C, G or T

<400> SEQUENCE: 15
acctctggca gttgggttca gggaaatggg attgncttgg ccttcaggct cctttggtca     60
taattttaaa atatgggagt ngaaaacaac naagaatgga atggnctntt aaaacaatga    120
aagagcnttt atcgnttgnc ccttgaatgn anaatttgnt tttgatttca taattctgct    180
ggtaaatgng acngttaaaa tgggccntta tgnatatata ttataattta naaatnccnt    240
tttataattt tactattcca gggngacnta atgcatttaa atttgggatt tgggnggngt    300
```

```
nttatgttta actggagttg ncaagtntga gtccctcang aaaaaaaaaa attctntttt    360
aaaaagcaat ctgattctta gctnttgaaa ctnttgctnc ttaaatttcc nataattaaa    420
aatttaaaat ttttaaatta gaattgccna tacttntacn tttganaagg g             471

<210> SEQ ID NO 16
<211> LENGTH: 295
<212> TYPE: DNA
<213> ORGANISM: Homo sapien

<400> SEQUENCE: 16
ggtcgcggcc gatgtaccat tgctttggcc ctgttagtgt cgcttgttgg aggtttgctt     60
tatttgagaa ggaacaactt ggagttcatc tataacaaga ctggttgggc catggtgtct   120
ctgtgtatag tctttgctat gacttctggc cagatgtgga accatatccg tggacctcca   180
tatgctcata agaacccaca caatggacaa gtgagctaca ttcatgggag cagccaggct   240
cagtttgtgg cagaatcaca cattattctg gtacctgccc gggcggccgc tcgaa        295

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
cgcggatccg tggccacaac catggtgagc aag                                  33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
ccgctcgagc ggagctagct tgccaaacct aca                                  33

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
cgcggatccg cgctgtcctc accatggcta                                      30

<210> SEQ ID NO 20
<211> LENGTH: 59
<212> TYPE: DNA
<213> ORGANISM: Artificial Sequence
<220> FEATURE:
<223> OTHER INFORMATION: primer

<400> SEQUENCE: 20
cgcggatccg cgggcgtagt cgggcacgtc gtaggggtat gaagttaaac actcctcaa     59

<210> SEQ ID NO 21
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 21
ggaagacacg gcttacctgg a                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 22
gatgcctagc cagttggtaa g                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 23
gcgattgcgc cagagacata g                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 24
gattcggtga tacgatcgcg a                                              21

<210> SEQ ID NO 25
<211> LENGTH: 23
<212> TYPE: DNA
<213> ORGANISM: Artificial Sequence
<220> FEATURE:
<223> OTHER INFORMATION: Synthetic sequence

<400> SEQUENCE: 25
cggtgtttcg tcctttccac aag                                            23
```